US008778633B2

(12) United States Patent
Lalonde et al.

(10) Patent No.: US 8,778,633 B2
(45) Date of Patent: Jul. 15, 2014

(54) TRANSCRIPTION FACTOR MODULATOR

(75) Inventors: Jean-Philippe Lalonde, Shenton Park (AU); Robin Scaife, Nedlands (AU); S. Peter Klinken, Mosman Park (AU)

(73) Assignee: Molecular Discover Systems, North Perth, Western Australia (AU)

( * ) Notice: Subject to any disclaimer, the term of this patent is extended or adjusted under 35 U.S.C. 154(b) by 0 days.

(21) Appl. No.: 13/310,196

(22) Filed: Dec. 2, 2011

(65) Prior Publication Data

US 2012/0164658 A1 Jun. 28, 2012

Related U.S. Application Data

(63) Continuation of application No. 12/296,256, filed as application No. PCT/AU2007/000459 on Apr. 5, 2007, now abandoned.

(30) Foreign Application Priority Data

Apr. 7, 2006 (AU) .................................. 2006901818
Apr. 7, 2006 (AU) .................................. 2006901820

(51) Int. Cl.
*C12Q 1/68* (2006.01)
*C12P 21/06* (2006.01)
*C07H 21/02* (2006.01)

(52) U.S. Cl.
USPC ........ 435/69.1; 435/6.1; 435/320.1; 536/23.1

(58) Field of Classification Search
USPC ...................... 435/6.1, 69.1, 320.1; 536/23.1
See application file for complete search history.

(56) References Cited

U.S. PATENT DOCUMENTS

| 4,935,493 | A | 6/1990 | Bachovchin et al. |
| 5,093,246 | A | 3/1992 | Cech et al. |
| 5,296,604 | A | 3/1994 | Hanko et al. |
| 5,462,928 | A | 10/1995 | Bachovchin et al. |
| 5,543,396 | A | 8/1996 | Powers et al. |
| 5,670,314 | A | 9/1997 | Christman et al. |
| 6,201,132 | B1 | 3/2001 | Jenkins et al. |
| 7,560,253 | B1 | 7/2009 | Klinken et al. |
| 8,148,343 | B2 | 4/2012 | Klinken et al. |
| 2002/0052308 | A1 | 5/2002 | Rosen et al. |
| 2010/0048450 | A1 | 2/2010 | Klinken et al. |
| 2010/0215637 | A1 | 8/2010 | Klinken et al. |
| 2010/0239649 | A1 | 9/2010 | Klinken et al. |

FOREIGN PATENT DOCUMENTS

| AU | 200115063 | 6/2001 |
| AU | 2006201164 | 4/2006 |
| EP | 0393457 | 7/1994 |
| EP | 0363284 | 5/1997 |
| EP | 0364344 | 5/1998 |
| WO | 88/04300 | 6/1988 |
| WO | 88/10266 | 12/1988 |
| WO | 90/11364 | 10/1990 |
| WO | 91/17171 | 11/1991 |
| WO | 99/38972 | 8/1999 |
| WO | 01/38374 | 5/2001 |
| WO | WO 02/12285 | 2/2002 |
| WO | WO 2007/041773 | 4/2007 |
| WO | 2007/109857 | 10/2007 |

OTHER PUBLICATIONS

Boggio et al., (2004), "A Mechanism for inhibiting the SUMO pathway," *Mol. Cell.*, 16(4):549-561.
Dohmen et al., (2004), "SUMO protein modification," *Biochim. Biophys. Acta*, 1695(1-3):113-131.
Written Opinion for International Application No. PCT/AU07/000459, mailed May 11, 2007 (7 pages).
International Search Report for International Application No. PCT/AU07/000459, mailed May 11, 2007 (6 pages).
Kimura et al., (2003), "Cloning and Characterization of a Novel Ring-B-box-Coiled-coil Protein with Apoptotic Function," *J. Biol. Chem.*, 278(27):25046-25054.
Lalonde et al., (2004), "HLS5, a Novel RBCC (Ring Finger, B Box, Coiled-coil) Family Member Isolated from a Hemopoietic Lineage Switch, is a Candidate Tumor Suppressor," *J. Biol. Chem.*, 279(9):8181-8189.
Abendroth et al., (2000), "Modulation of major histocompatibility class II protein expression by varicella-zoster virus," *J. Virol.*, 74(4):1900-7.
Agarwal et al., (1998), "The p53 network," *J. Biol. Chem.*, 273(1):1-4.
Amit et al., (2003), "NF-kappaB activation in cancer: a challenge for ubiquitination- and proteasome-based therapeutic approach," *Semin Cancer Biol.*, 13(1):15-28.
Angelastro et al., (1990), "Alpha-diketone and alpha-keto ester derivatives of N-protected amino acids and peptides as novel inhibitors of cysteine and serine proteinases," *J. Med. Chem.*, 33(1):11-3.
Angliker et al., (1987), "The synthesis of lysylfluoromethanes and their properties as inhibitors of trypsin, plasmin and cathepsin B, " *Biochem J.*, 241(3):871-5.
Been et al., (1986), "One binding site determines sequence specificity of Tetrahymena pre-rRNA self-splicing, trans-splicing, and RNA enzyme activity," *Cell.*, 47(2):207-16.
Ben-Neriah, (2002), "Regulatory functions of ubiquitination in the immune system," *Nat. Immunol.*, 3(1):20-6.
Berti et al., (2004), "Mig12, a novel Opitz syndrome gene product partner, is expressed in the embryonic ventral midline and co-operates with Mid1 to bundle and stabilize microtubules," *BMC Cell Biol.*, 5:9.
Brés et al., (2003), "A non-proteolytic role for ubiquitin in Tat-mediated transactivation of the HIV-1 promoter," *Nat. Cell. Biol.*, 5(8):754-61.
Chorev et al., (1993), "A dozen years of retro-inverso peptidomimetics," *Acc. Chem. Res.*, 26:266-273.

(Continued)

Primary Examiner — Karen Cochrane Carlson
(74) Attorney, Agent, or Firm — K&L Gates LLP

(57) ABSTRACT

The present invention relates to novel agents that are useful for modulating transcription factor activity. In particular, the present invention relates to a transcription factor modulator comprising (i) a pharmaceutically-effective amount of a HLS-5 polypeptide, isoform thereof, functional fragment thereof or pharmaceutical composition thereof or (ii) a compound or composition capable of regulating the endogenous levels of HLS-5 or its activity; or (iii) combinations thereof.

7 Claims, 10 Drawing Sheets

(56) References Cited

OTHER PUBLICATIONS

Ciechanover et al., (2000), "Ubiquitin-mediated proteolysis: biological regulation via destruction," *Bioessays.*, 225:442-51.
de Théet al., (1991), "The PML-RAR alpha fusion mRNA generated by the t(15;17) translocation in acute promyelocytic leukemia encodes a functionally altered RAR," *Cell.*, 66(4):675-84.
Deng et al., (2000), "Activation of the IkappaB kinase complex by TRAF6 requires a dimeric ubiquitin-conjugating enzyme complex and a unique polyubiquitin chain," *Cell*, 103(2):351-61.
Deshaies et al., (1999), "SCF and Cullin/Ring H2-based ubiquitin ligases," *Annu. Rev. Cell Dev. Biol.*, 15:435-67.
Diamonti et al., (2002), "An RBCC protein implicated in maintenance of steady-state neuregulin receptor levels," *Proc. Natl. Acad. Sci. U.S.A.*, 99(5):2866-71.
Duprez et al., (1999), "SUMO-1 modification of the acute promyelocytic leukaemia protein PML: implications for nuclear localisation," *J. Cell. Sci.*, 112 ( Pt 3):381-93.
Dupuis et al., (2000), "Human interferon-gamma-mediated immunity is a genetically controlled continuous trait that determines the outcome of mycobacterial invasion," *Immunol. Rev.*, 178:129-37.
Dupuis et al., (2003), "Impaired response to interferon-alpha/beta and lethal viral disease in human STAT1 deficiency," *Nat. Genet*, 33(3):388-91.
Ewoldt et al., (1992), "Sulfonyl fluoride serine protease inhibitors inactivate RNK-16 lymphocyte granule proteases and reduct lysis by granule extracts and perforin," *Mol. Immunol.*, 29(6):713-21.
Ferdous et al., (2001), "The 19S regulatory particle of the proteasome is required for efficient transcription elongation by RNA polymerase II," *Mol. Cell.*, 7(5):981-91.
Flick et al., (2004), "Proteolysis-independent regulation of the transcription factor Met4 by a single Lys 48-linked ubiquitin chain," *Nat. Cell. Biol.*, 6(7):634-41.
Gallop et al., (1994), "Applications of combinatorial technologies to drug discovery 1. Background and peptide combinatorial libraries," *J. Med. Chem.*, 37(9):1233-51.
Green et al., (1981), "Peptidyl diazomethyl ketones are specific inactivators of thiol proteinases," *J. Biol. Chem.*, 256(4):1923-8.
Haseloff et al., (1988), "Simple RNA enzymes with new and highly specific endoribonuclease activities," *Nature*, 334(6183):585-91.
Hatakeyama et al., (2001), "U box proteins as a new family of ubiquitin-protein ligases," *J. Biol. Chem.*, 276(35):33111-20.
Hay, (2001), "Protein modification by SUMO," *Trends Biochem. Sci.*, 26(5):332-3.
Hernandez et al., (1992), "Effect of the 7-amino substituent on the inhibitory potency of mechanism-based isocoumarin inhibitors for porcine pancreatic and human neutrophil elastases: a 1.85-A X-ray structure of the complex between porcine pancreatic elastase and 7-[(N-tosylphenylalanyl)amino]-4-chloro-3-methoxyisocoumarin," *J. Med. Chem.*, 35(6):1121-9.
Hershko et al., (1998), "The ubiquitin system," *Annu. Rev. Biochem.*, 67:425-79.
Hershko et al., (2000), "Basic Medical Research Award. The ubiquitin system," *Nat. Med.*, 6(10):1073-81.
Hochstrasser, (2000), "Evolution and function of ubiquitin-like protein-conjugation systems," *Nat. Cell. Biol.*, (8):E153-7.
Hudig et al., (1989), "Selective isocoumarin serine protease inhibitors block RNK-16 lymphocyte granule-mediated cytolysis," *Mol. Immunol.*, 26(8):793-8.
Hudig et al., (1991), "The function of lymphocyte proteases. Inhibition and restoration of granule-mediated lysis with isocoumarine serine protease inhibitors," *J. Immunol.*, 147(4):1360-8.
Jackson et al., (2000), "The lore of the Rings: substrate recognition and catalysis by ubiquitin ligases," *Trends Cell. Biol.*, 10(10):429-39.
Jentsch et al., (2000), "Ubiquitin and its kin: how close are the family ties?," *Trends Cell Biol.*, 10(8):335-42.
Kaiser et al., (2000), "Regulation of transcription by ubiquitination without proteolysis: Cde34/SCF(Met30)-mediated inactivation of the transcription factor Met4," *Cell.*, 102(3):303-14.

Kajiwara et al., (1987), "Elucidation of calpain dependent phosphorylation of myosin light chain in human platelets," *Biochem Int.*, 15(5):935-44.
Kam et al., (1988), "Mechanism-based isocoumarin inhibitors for trypsin and blood coagulation serine proteases: new anticoagulants," *Biochemistry*, 27(7):2547-57.
Kam et al., (1990), "Thioester chromogenic substrates for human factor VIIa: substituted isocoumarins are inhibitors of factor VIIa and in vitro anticoagulants," *Thromb Haemost.*, 64(1):133-7.
Kawakami et al., (2001), "NEDD8 recruits E2-ubiquitin to SCF E3 ligase," *Embo. J.*, 20(15):4003-12.
Keil et al., (1995), "Emergence of myeloid cells from cultures of J2E erythroid cells is linked with karyotypic abnormalities," *Cell Growth Differ.*, 6(4):439-48.
Kimura et al., (2003), "Cloning and characterization of a novel Ring-B-box-coiled protein with apoptitic function," *J. Biol. Chem.*, 278(27):25046-54.
Klinken et al., (1988), "In vitro-derived leukemic erythroid cell lines induced by a raf- and myc-containing retrovirus differentiate in response to erythropoietin," *Proc. Natl. Acad. Sci. U.S.A.*, 85(22):8506-10.
Kloetzel, (2001), "Antigen processing by the proteasome," *Nat. Rev. Mol. Cell. Biol.*, 2(3):179-87.
Kondo et al., (2001), "The von Hippel-Lindau tumor suppressor gene," *Exp. Cell Res.*, 264(1):117-25.
Kuras et al., (2002), "Dual regulation of the met4 transcription factor by ubiquitin-dependent degradation and inhibition of promoter recruitment," *Mol. Cell.*, 19(1):69-80.
Lakin et al., (1999), "Regulation of p53 in response to DNA damage," *Oncogene*, 18(53):7644-55.
Lalonde et al., (2004), "HLS5, a novel RBCC (ring finger, B box, coiled-coil) family member isolated from a hemopoietic lineage switch, is a candidate tumor suppressor," *J. Biol. Chem.*, 279(9):8181-9.
Lin et al., (2004), "Association of Ubc9, an E2 ligase for SUMO conjugation, with p53 is regulated by phosphorylation of p53," *Febbs. Lett.*, 573(1-3):15-8.
Liu et al., (2005), "Negative regulation of NF-kappaB signaling by PIAS1," *Mol. Cell Biol.*, 25(3):1113-23.
Mahajan et al., (1997), "A small ubiquitin-related polypeptide involved in targeting RanGAP1 to nuclear pore complex protein RanBP2," *Cell.*, 88(1):97-107.
McCaffrey et al., (2002), "RNA interference in adult mice," *Nature*, 418(6893):38-9.
McManus et al., (2002), "Gene silencing using micro-RNA designed hairpins," *RNA*, 8(6):842-50.
Meek, (1999), "Mechanisms of switching on p53: a role for covalent modification?," *Oncogene*, 18(53):7666-75.
Megidish et al., (2002), "Activation of p53 by protein inhibitor of activated Stat1 (PIAS1)," *J. Biol. Chem.*, 277(10):8255-9.
Meroni et al., (2005), "TRIM/RBCC, a novel class of 'single protein Ring finger' E3 ubiquitin ligases," *Bioessays*, 27(11):1147-57.
Miller et al., (1998), "Human cytomegalovirus inhibits major histocompatibility complex class II expression by disruption of the Jak/Stat pathway," *J. Exp. Med.*, 187(5):675-83.
Morrison et al., (2001), "Inhibition of IFN-gamma signaling by an Epstein-Barr virus immediate-early protein," *Immunity*, 15(5):787-99.
Muller et al., (2000), "c-Jun and p53 activity is modulated by SUMO-1 modification," *J. Biol. Chem.*, 275(18):13321-9.
Odake et al., (1991), "Human and murine cytotoxic T lymphocyte serine proteases: subsite mapping with peptide thioester substrates and inhibition of enzyme activity and cytolysis by isocoumarins," *Biochemistry*, 30(8):2217-27.
Olson et al., (1993), "Concepts and progress in the development of peptide mimetics," *J. Med. Chem.*, 36(21):3039-49.
Orlowski et al., (1989), "Substrate specificity and inhibitors of a capillary injury-related protease from sheep lung lymph," *Arch Biochem. Biophys.*, 269(1):125-36.
Oweida et al., (1990), "In vivo determination of the anticoagulant effect of a substituted isocoumarin (ACITIC)," *Thromb Res.*, 58(2):191-7.

(56) References Cited

OTHER PUBLICATIONS

Paddison et al., (2002), "Short hairpin RNAs (shRNAs) induce sequence-specific silencing in mammalian cells," *Genes Dev.*, 16(8):948-58.
Parkes et al., (1985), "Calpain inhibition by peptide epoxides," *Biochem J.*, 230:509-516.
Pearson et al., (2000), "PML regulates p53 acetylation and premature senescence induced by oncogenic Ras," *Nature*, 406(6792):207-10.
Powers et al., (1989), "Mechanism-based isocoumarin inhibitors for serine proteases: use of active site structure and substrate specificity inhibitor design," *J. Cell Biochemistry*, 39(1):33-46.
Powers et al., (1990), "Reaction of porcine pancreatic elastase with 7-substituted 3-alkoxy-4-chloroisocoumarins: design of potent inhibitors using the crystal structure of the complex formed with 4-chloro-3-ethoxy-7-guanidinoisocoumarin," *Biochemistry*, 29(12):3108-18.
Puri et al., (1989), "Thrombin-induced platelet aggregation involves an indirect proteolytic cleavage of aggregin by calpain," *Arch Biochem. Biophys.*, 271(2):346-58.
Read et al., (2000), "Nedd8 modification of of cul-1 activates SCF(beta(TrCP))-dependent ubiquitination of IkappaBalpha," *Mol. Cell Biol.*, 20(7):2326-33.
Reymond et al., (2001), "The tripartite motif family identifies cell compartments," *Embo. J.*, 20(9):2140-51.
Rodriguez et al., (1999), "SUMO-1 modification activates the transcriptional response of p53," *Embo J.*, 18(22):6455-61.
Sarver et al., (1990), "Ribozymes as potential anti-HIV-1 therapeutic agents," *Science*, 2427(4947):1222-5.
Saxena et al., (2004), "A dimerized coiled-coil domain and an adjoining part of geminin interact with two sites on Cdt1 for replication inhibition," *Mol. Cell.*, 15(2):245-58.
Schmidt et al., (2002), "Members of the PIAS family act as SUMO ligases for c-Jun and p53 and repress p53 activity," *Proc. Natl. Acad. Sci. U.S.A.*, 99(5):2872-7.
Schoser et al., (2005), "Commonality of TRIM32 mutation in causing sarcotubular myopathy and LGMD2H," *Ann. Neurol.*, 57(4):591-5.
Schwartz et al., (2003), "A superfamily of protein tags: ubiquitin, SUMO and related modifiers," *Trends Biochem. Sci.*, 28(6):321-8.
Shmueli et al., (2005), "Life, death, and ubiquitin: taming the mule," *Cell.*, 121(7):963-5.
Sionov et al., (1999), "The cellular response to p53: the decision between life and death," *Oncogene*, 18(45):6145-57.
Townsend et al., (2004), "STAT-1 interacts with p53 to enhance DNA damage-induced apoptosis," *J. Biol. Chem.*, 279(7):5811-20.
Tsujinaka et al., (1988), "Synthesis of a new cell penetrating calpain inhibitor (calpeptin)," *Biochem. Biophys. Res. Commun.*, 153(3):1201-8.
Urano et al., (2002), "Efp targets 14-3-3 sigma for proteolysis and promotes breast tumour growth," *Nature*, 417(6891):871-5.
Vijayalakshmi et al., (1991), "Structural study of porcine pancreatic elastase complexed with 7-amino-3-(2-bromoethoxy)-4-chloroisocoumarin as a nonreactivatable double covalent enzyme-inhibitor complex," *Biochemistry*, 30(8):2175-83.
Vlasak et al., (1989), "Influenza C virus esterase: analysis of catalytic site, inhibition, and possible function," *J. Virol.*, 63(5):2056-62.
Wang et al., (2001), "TAK1 is a ubiquitin-dependent kinase of MKK and IKK," *Nature*, 412(6844):346-51.
Weissman, (2001), "Themes and variations on ubiquitylation," *Nat. Rev. Mol. Cell. Biol.*, 2(3):169-78.
Welte et al., (2003), "STAT3 deletion during hematopoiesis causes Crohn's disease-like pathogenesis and lethality: a critical role of STAT3 in innate immunity," *Proc. Natl. Acad. Sci U.S.A.*, 100(4):1879-84.
Williams et al., (1999), "HLS7, a hemopoietic lineage switch gene homologous to the leukemia-inducing gene MLF1," *Embo. J.*, 18(20):5559-66.
Xu et al., (2003), "BTBD1 and BTBD2 colocalize to cytoplasmic bodies with the RBCC/tripartite motif protein, TRIM5delta," *Exp. Cell Res.*, 288(1):84-93.
Yap et al., (2005), "A single amino acid change in the SPRY domain of human Trim5alpha leads to HIV-1 restriction," *Curr. Biol.*, 15(1):73-8.
Yewdell, (2001), "Not such a dismal science: the economics of protein synthesis, folding, degradation and antigen processing," *Trends Cell Biol.*, 11(7):294-7.
Yu et al., (2002), "RNA interference by expression of short-interfering RNAs and hairpin RNAs in mammalian cells," *Proc. Natl. Acad. Sci. U.S.A.*, 99(9):6047-52.
Zachariae et al., (1999), "Whose end is destruction: cell division and the anaphase-promoting complex," *Genes Dev.*, 13(16):2039-58.
Zaug et al., (1984), "A labile phosphodiester bond at the ligation junction in a circular intervening sequence RNA," *Science*, 224(4649):574-8.
Zaug et al., (1986), "The intervening sequence RNA of Tetrahymena is an enzyme," *Science*, 231(4737):470-5.
Zaug et al., (1986), "The Tetrahymena ribozyme acts like an RNA restriction endonuclease," *Nature*, 324(6096):429-33.
Zunino et al., (1988), "Localization, implications for function, and gene expression of chymotrypsin-like proteinases of cytotoxic RNK-16 lymphocytes," *Biochim. Biophys. Acta.*, 967(3):331-40.
Database Fasta (Online) Aug. 4, 1999 Kikuno et al. Prediction of the coding sequences of unidentified human genes. XIV. The complete sequences of 100 new CDNA clones from brain which codes for large proteins in vitro. Retrieved from EMBL Database accession No. AB029021 XP002274849.
Database Fasta (Online) May 1, 2000 Kikuno et al. Prediction of the coding sequences of unidentified human genes. XIV. The complete sequences of 100 new CDNA clones from brain which codes for large proteins in vitro. Retrieved from EMBL Database accession No. Q9UPQ4 XP002274850.
Kikuno et al., Prediction of the coding sequences of unidentified human genes XIV. The complete seuqneces of 100 new DNA Clones from brain which code for large proteins in vitro, *DNA Res.*,vol. 6, No. 3, Jun. 3, 1999, pp. 197-205.
Klinken et al., Hemopoietic linkage switch: v-raf oncogene coverts Emu-myc transgenic B cells into macrophages, *Cell*, vol. 53, Jun. 7, 1988 pp. 857-867.

SEQUENCE LISTING

```
<160> NUMBER OF SEQ ID NOS: 15

<210> SEQ ID NO 1
<211> LENGTH: 3687
<212> TYPE: DNA
<213> ORGANISM: Mus musculus

<400> SEQUENCE: 1
tcagcaggga caacgcccgc aggctaggca tgaaggcggc gacaccggtg gtggtgacgg      60
cggctgctcc tgcgatggag ccgggccctt ctgtgtcccc ggggccttcg cgctccttca     120
aagaggagct gctgtgtgcc gtgtgctacg acccgttccg cgacgcagta actctgcgct     180
gtggccacaa cttctgccgc cggtgcgtga gcggctgctg ggaggtgcag acgacgccct     240
cgtgtccggt gtgcaaggaa cgagcggtgc ccggggagct gcgcaccaac cacacgctca     300
acaacctggt ggagaccttg ctgcgcgagg aggctgaggg cgcgcgctgg accggtcgcc     360
ggtccccgcg cccctgccgt gcgcaccgtg ccccgctcac gctcttctgc ctggaggaca     420
aggagctgct gtgctgtgct tgccaggccg acgcccggca ccaagagcat cgtgtgcagc     480
ccatcaagga cactgcgcaa gacttccggg ccaagtgtaa gaacatggag catgtattgc     540
gagagaaagc caaggccttc tgggccctga ggcgcaccta tgaggccatt gccaagcaca     600
atgaggtgca aacgacttgg ctggaaggcc gcatccggga tgagtttgac aagctccgtg     660
atttcctgag ggtggaggaa caggccacct tggatgccat gaaggaagag agcagaaaga     720
agcacctgca ggctgaggag aagatgaagc agctagcaga acagaccgag gcgctggctc     780
gggagattga gcgtctgcag atggagatga aggaagatga catgaccttc ctcatgaaac     840
acaagagccg aaaacgccgg ctcttctgca ccgtggagcc agctcctctc cagcctggct     900
tgctaatgga tgcatgcaag tatctggagt ccctgcagta ccgagtctgg aagaagatgc     960
```

```
ttggatccgt tgagtctgtg cccttcagct tggatcccaa cacagctgct ggctggctca   1020
aagtggctga tgacctcacg agtgtcatca accatggcta ccgcgtgcaa gtggagaatc   1080
cagagcgctt ctcctcggca ccctgcctgc taggctctca agtgttctcc aagggctccc   1140
actcttggga ggtggatgtg ggtggcctgc caacctggcg agtgggtgtg gttcgggtgc   1200
aggcacatgc acaggcgcag gctcaggctg acgtaggtgg tgaaggccac tcacacagct   1260
gctaccatga tacacgctca ggcttctggt acctgtgccg cacgcagggt gtggatggag   1320
accactgcat gacttccgac actgccacag cccctctggt ccaggccatg ccgcgccgtc   1380
tgcgtgtgga gctggagtgt gaggagggtg agctatcctt ctatgactct gagcgccact   1440
gccatctgta taccttccat gcccactttg ggaggtgag gccctacttc tacctgggag    1500
cctctcgagg tgacggtccc ccggaacctc tgcgtatctg ccacctgcgt gtctccatca   1560
aagaagagct ggacatctga gctgcccacc cctgacacat gcagcatact atatcctgtc   1620
ttagcttttc tgtagctcca aagttaggag ccacccagga ggtgcttggc tgagcctagg   1680
ctctgtctac agtcatgcta ccttcaggat gtgggttttc tgttcttgga ttgctggtat   1740
actgttttct tgtaggatg gcattataat gtaggtgtag actattttta gagatgatga    1800
agccagccta tcaggagatg cctcttattg agtctatttg tcatttatgt ttcccaggaa   1860
gaggtccttg tcaggccaca cagggaagcc ccaggatggt ttgagacaag agtgggcaaa   1920
gccttcacct aggctctccc accccagtag gacaagttag gtattggcca gcctcactga   1980
gctatgcatg gctttagcat ctggtctgaa ccaggagtcc ccgtgttggt tcctaggaca   2040
ggattgtcct tgactctctc tgtgggaaca ctgtagggtg tgaggtactc tggaatacag   2100
ctcagagttg tgggtgtctc aggaaaggca gctccagggc cttggcagt ggttaaggac    2160 tgaccagcct caagttagtg ccatagaggc caaagcacca gaatgcagtg agtgagaaga   2220
cagctagtgc tgggttggaa catgagcccc actctgttac tcagtctttc ggcacggaat   2280
cgacactggt tggtcacctc atgctttgaa cgtttcctct ggaattgtcc agttttctag   2340 aacactttt aaacctgtgt ttccacatct gtgatttgac actagtcctt ggaaatcact    2400
ggaggaaggt atgagaagga gcctcagaga atgctgcttc agtcagtgac tgttggtctg   2460
ggagacgagt cctggccttg ctggccgttg tcttcattgg cttccacctg cctgtccttg   2520
ctctgctctc tgcagattcc acccctttcc tttatgtgtc cctctgcctt tctttctca    2580 gtcatgcctg tagatggagt ctaattgcca actaaccaaa tcccaagaga tgttgtaagg   2640
aaaaaatacc atctcagggg tgccctgtca tcgtcaagac ctaggaccta gcatcccaat   2700
ttcagcctgc accctcatt acataagact tgttttaaac cacgccgatt acccactaat    2760
tggctctaaa tgggtcatgt gcacttgtgg attatctaac aagtggagac acagaagaaa   2820
ccctggtgca ggccaggccg ggagcaggga cagtgttggc aagccagctt gtgagtgtca   2880
gatgcttggg caccacggat gtgaaaggtg cgcctggtgc aatgtatgtg tttggttaaa   2940
gaaactctct gaaattactg ttataataag ttttttaaaag ttttttcttt cttttttaatt  3000 ttcaccttaa ctcttaaata gggtaatttc aatgacctag actcttagaa aaaatttgac   3060
ttaccccaca actgacatgt ttcttttcaga gcttttgtaa acacaaattc ctagtgtaac   3120
ttgtacctga tctgtccttc ccattgtaag attccatcgt gtgcagtgaa tgtgctgtgc   3180
aacttgttag ttgatggaca tttggcttgt tgcagtgtgt ttagctgtta tgagttctgc   3240
tgctatgaaa tttgtgtgca agttttgtgt ggctgtgtct cttgattttc tgtcatatac   3300
```

```
cttggagtct gttttccagg tcatatgata attattttaa gcccttttggg gacttgccaa    3360 gctgtttcta agagagccgt cccatttctc actcccaccg gcagcaggtg agggctggtt    3420
tgtaacgaat tctctctgcc ctcttaagct gaggaagctg gagtaggtct catttgccct    3480
gtagttgcga tctctgatgg ctggggagca tctttcctca tgtttgctgt gtatctgctt    3540
cagagacttc agggtgtttg cccattgggt tgtctgacct tttattatga aggtttacaa    3600
gtttgttatg cattctagat aaagttcct ttgtgtcaga tgaatcacat aaaaattttc    3660
ctcctaattc aaaaaaaaaa aaaaaaa                                          3687
```

<210> SEQ ID NO 2
<211> LENGTH: 501
<212> TYPE: PRT
<213> ORGANISM: Mus musculus

<400> SEQUENCE: 2

```
Met Glu Pro Gly Pro Ser Val Ser Pro Gly Pro Ser Arg Ser Phe Lys
 1               5                  10                  15

Glu Glu Leu Leu Cys Ala Val Cys Tyr Asp Pro Phe Arg Asp Ala Val
             20                  25                  30

Thr Leu Arg Cys Gly His Asn Phe Cys Arg Arg Cys Val Ser Gly Cys
         35                  40                  45

Trp Glu Val Gln Thr Thr Pro Ser Cys Pro Val Cys Lys Glu Arg Ala
     50                  55                  60

Val Pro Gly Glu Leu Arg Thr Asn His Thr Leu Asn Asn Leu Val Glu
 65                  70                  75                  80

Thr Leu Leu Arg Glu Glu Ala Glu Gly Ala Arg Trp Thr Gly Arg Arg
                 85                  90                  95

Ser Pro Arg Pro Cys Arg Ala His Arg Ala Pro Leu Thr Leu Phe Cys
            100                 105                 110

Leu Glu Asp Lys Glu Leu Leu Cys Cys Ala Cys Gln Ala Asp Ala Arg
        115                 120                 125

His Gln Glu His Arg Val Gln Pro Ile Lys Asp Thr Ala Gln Asp Phe
    130                 135                 140

Arg Ala Lys Cys Lys Asn Met Glu His Val Leu Arg Glu Lys Ala Lys
145                 150                 155                 160

Ala Phe Trp Ala Leu Arg Arg Thr Tyr Glu Ala Ile Ala Lys His Asn
                165                 170                 175

Glu Val Gln Thr Thr Trp Leu Glu Gly Arg Ile Arg Asp Glu Phe Asp
            180                 185                 190

Lys Leu Arg Asp Phe Leu Arg Val Glu Glu Gln Ala Thr Leu Asp Ala
        195                 200                 205

Met Lys Glu Glu Ser Arg Lys Lys His Leu Gln Ala Glu Glu Lys Met
    210                 215                 220

Lys Gln Leu Ala Glu Gln Thr Glu Ala Leu Ala Arg Glu Ile Glu Arg
225                 230                 235                 240

Leu Gln Met Glu Met Lys Glu Asp Asp Met Thr Phe Leu Met Lys His
                245                 250                 255

Lys Ser Arg Lys Arg Arg Leu Phe Cys Thr Val Glu Pro Ala Pro Leu
            260                 265                 270

Gln Pro Gly Leu Leu Met Asp Ala Cys Lys Tyr Leu Glu Ser Leu Gln
        275                 280                 285

Tyr Arg Val Trp Lys Lys Met Leu Gly Ser Val Glu Ser Val Pro Phe
    290                 295                 300
```

Ser Leu Asp Pro Asn Thr Ala Ala Gly Trp Lys Val Ala Asp Asp
305                 310                 315                 320

Leu Thr Ser Val Ile Asn His Gly Tyr Arg Val Gln Val Glu Asn Pro
            325                 330                 335

Glu Arg Phe Ser Ser Ala Pro Cys Leu Leu Gly Ser Gln Val Phe Ser
        340                 345                 350

Lys Gly Ser His Ser Trp Glu Val Asp Val Gly Gly Leu Pro Thr Trp
    355                 360                 365

Arg Val Gly Val Val Arg Val Gln Ala His Ala Gln Ala Gln Ala Gln
370                 375                 380

Ala Asp Val Gly Gly Glu Gly His Ser His Ser Cys Tyr His Asp Thr
385                 390                 395                 400

Arg Ser Gly Phe Trp Tyr Leu Cys Arg Thr Gln Gly Val Asp Gly Asp
            405                 410                 415

His Cys Met Thr Ser Asp Thr Ala Thr Ala Pro Leu Val Gln Ala Met
        420                 425                 430

Pro Arg Arg Leu Arg Val Glu Leu Glu Cys Glu Gly Glu Leu Ser
    435                 440                 445

Phe Tyr Asp Ser Glu Arg His Cys His Leu Tyr Thr Phe His Ala His
450                 455                 460

Phe Gly Glu Val Arg Pro Tyr Phe Tyr Leu Gly Ala Ser Arg Gly Asp
465                 470                 475                 480

Gly Pro Pro Glu Pro Leu Arg Ile Cys His Leu Arg Val Ser Ile Lys
            485                 490                 495

Glu Glu Leu Asp Ile
            500

<210> SEQ ID NO 3
<211> LENGTH: 4196
<212> TYPE: DNA
<213> ORGANISM: Homo sapiens

<400> SEQUENCE: 3
ctcgggtcgc gggcgttggc agccgggcgg gtgggagggg ccggagcaaa agttccgggc      60
gcccgagccg gctgctcgtg ccatggagcg gagtcccgac gtgtccccg ggccttcccg      120 ctccttcaag gaggagttgc tctgcgccgt ctgctacgac cccttccgcg acgcagtcac      180
tctgcgctgc ggccacaact tctgccgcgg gtgcgtgagc cgctgctggg aggtgcaggt      240
gtcgcccacc tgcccagtgt gcaaagaccg cgcgtcaccc gccgacctgc gcaccaacca      300 cacctcaac aacctggtgg agaagctgct gcgcgaggag gccgagggcg cgcgctggac      360
cagctaccgc ttctcgcgtg tctgccgcct gcaccgcgga cagctcagcc tcttctgcct      420
cgaggacaag gagctgctgt gctgctcctg ccaggccgac cccgacaccc aggggcaccg      480
cgtgcagccg gtgaaggaca ctgcccacga ctttcgggcc aagtgcagga acatggagca      540
tgcactgcgg agaaggcca aggccttctg ggcatgcgg cgctcctatg aggccatcgc      600
caagcacaat caggtggagg ctgcatggct ggaaggccgg atccggcagg agtttgataa      660
gcttcgcgag ttcttgagag tggaggagca ggccattctg gatgccatgg ccgaggagac      720
aaggcagaag caacttctgg ccgacgagaa gatgaagcag ctcacagagg agacggaggt      780
gctggcacat gagatcgagc ggctgcagat ggagatgaag gaggacgacg tttcttttct      840
catgaaacac aagagccgaa aacgccgact cttctgcacc atggagccag agccagtcca      900
gcccggcatg cttatcgatg tctgcaagta cctgggctcc ctgcagtacc gcgtctggaa      960

```
gaagatgctt gcatctgtgg aatctgtacc cttcagcttt gaccccaaca ccgcagctgg    1020
ctggctctcc gtgtctgacg acctcaccag cgtcaccaac catggctacc gcgtgcaggt    1080
ggagaacccg gaacgcttct cctcggcgcc ctgcctgctg ggctcccgtg tcttctcaca    1140
gggctcgcac gcctgggagg tggcccttgg ggggctgcag agctggaggg tgggcgtggt    1200
acgtgtgcgc caggactcgg gcgctgaggg ccactcacac agctgctacc acgacacacg    1260
ctcgggcttc tggtatgtct gccgcacgca gggcgtggag ggggaccact gcgtgacctc    1320
ggacccagcc acgtcgcccc tggtcctggc catcccacgc cgcctgcgtg tggagctgga    1380
gtgtgaggag ggcgagctgt ctttctatga cgcggagcgc cactgccacc tgtacacctt    1440
ccacgcccgc tttggggagg ttcgccccta cttctacctg gggggtgcac ggggcgccgg    1500
gcctccagag cctttgcgca tctgcccctt gcacatcagt gtcaaggaag aactggatgg    1560
ctgagctggc ccggggctgc cccggtcttg tgccacagca ctgttttctt tctgccctct    1620
tcctaatgcc cacactgctt gggcactatt gcgcccctgc ctccttgcca ggctcttcct    1680
cctgtcctgc ctggtccttt tccatgactc caggctgtgc ctctctccat gtttggtccc    1740
ttctgtgccc atggtcagga gctattcggg tggcacctcg ctggccaggc tctcccgagt    1800
cgtggcacct ccacaatgtg aattttctga atccctattc caggatttct gggaataatg    1860
tttacttcta gaatgggcct gttgtaaacc atctcatcga ggtgtggtaa agccattgga    1920
tgaggagggg actgccatgg aaaggagagt ttgttactta cggttctgag aggaggggcc    1980
acataggaaa gccccacggt gggtcagaag gcggaaggag ggaggggaac gtgtgggcaa    2040
gagacttcct ctggtttcct caggaggaaa tgggcaaggc agagtaagca ggggagacag    2100
gtttaagggt agctggcttg agtaatttca gtggctctca ggatagggc tgccctttttt    2160 gtctgatacc tggcccccggg atagtcagga caggtgaatg ttggcctggg gtgtgacagc    2220
cctgggagag ccatgtgaag gaggcagctg gcgccatcgc tccggattag ttggtttcca    2280
taggaaaggc atgctttcag ccagatgctt gccatctcta gggattgggg gattggctag    2340
cctgggagga tcagtctgtc caggtcagcg aggccccaga taccagagca tcaagagtac    2400
aggaaataca gttaatgcag ggcctctgtg tggctggatc ctccgtctcc atcagatcag    2460
ctctgattga tctattcttg cacgatttcc tctgaacaca gggttccaga gtacttaaac    2520
acaacatttt ttaaatcgtg atttcggcct atttccttgc caggcctgtt tccccaccag    2580
gaaatgagat aggaggactg gatgaggatg tcctgttata gttgctgtgg aggaagttcc    2640
tctggttaat tctcatcagc gtctgcagaa aagaaggaaa gagggcaccc ttttcagttg    2700
ggaagaaagg agaggggtgg cgccatggac gtggccctaa acgctgtggg agagggaaga    2760
ggaggctggg cctcgctgcc ctcttgtctc tgctgacttc agcctggtca tgcttgctct    2820
gccacttgcg atttcatccc taatttcttc ctccaccatg cctgcagact tttccctggg    2880
cttgtttttt ctcgcacatc tctgaagagt ttttaatctt cagctcatca tgtcccagga    2940
agtggcatca taaaaggaaa tatttttttt tcctaggagc agtgttaaaa tctgggtcac    3000
attcctgacc aaggacagca tcctgccttc tgcccatccc cttcagttca caaaagctga    3060
cattttaaac aaatcatgac tcacacgtat taattggtta taaatatgtt gtgtacactg    3120
gttagataaa acttaaggcc acaaggaggg cccaggtagg cgatgtcagt gtgtgaaggg    3180
gctggattgg gcgtggtgag gatgttggca aaccagtgca tgcacctggt tggaagatgc    3240
tcagcctcac aaaagctcca agcccttggg gagccaaagt gtctgagagt gtgaccctct    3300
cctgtaaagt atttatccca cccattaata taatttctgt ataataaact tgacctgaaa    3360
```

-continued

```
ttatttcatt ctttatatta aacttttaaa aatgtttttt attttcacct tagatatggg    3420
aagagttttt tttttttttt tttttttttta acaggataac ttgagcaggc taggcctctt    3480
aaaaaaaaat ttgagctaaa actcatttt cttttggcat tttcttttca atgttcttat    3540
aagcaaagtt catccatgtt gtagcatgtg ttcaacttta ttttttcatc gggtaatatt    3600
ccattgtatg gaatggtagt actacatttt atttatcatg catcgattgg tggacatttg    3660
gatcgtttct acttcttgac tattatacat aatgctgcta ggaacttttg tgtatgagtt    3720
tttgtgtgga catatgtttt catttctctt tggtatatgc ctgggagcag atttgctgga    3780
tcatatgaaa ctctatttaa cccttgaggg actcccaaac tgttttccaa tgtggtgaca    3840 caatttata tcccatcaac agggcatgag ggttctgatg actccacatc cctcagtgct    3900
ttttattatc tatctttaa cttagccatc ctagtagggg taatgtggca tctcattgtg    3960
attttggttt gcatttccct gatggcgaat gatattgagc atcttttcat gagcttattg    4020
gccattgcca tatcttctta ggacagctat ctttagatca cttgctcatt ttttaattgg    4080
gttatttgtc tttttattat tgagttgtaa gagtcctttt atagcctggc acaagtccct    4140
ttaactggta tatgattata aaattttct ccgtgagctg tttcatttcc ttgatg         4196
```

<210> SEQ ID NO 4
<211> LENGTH: 493
<212> TYPE: PRT
<213> ORGANISM: Homo sapiens

<400> SEQUENCE: 4

```
Met Glu Arg Ser Pro Asp Val Ser Pro Gly Pro Ser Arg Ser Phe Lys
1               5                   10                  15

Glu Glu Leu Leu Cys Ala Val Cys Tyr Asp Pro Phe Arg Asp Ala Val
            20                  25                  30

Thr Leu Arg Cys Gly His Asn Phe Cys Arg Gly Cys Val Ser Arg Cys
        35                  40                  45

Trp Glu Val Gln Val Ser Pro Thr Cys Pro Val Cys Lys Asp Arg Ala
    50                  55                  60

Ser Pro Ala Asp Leu Arg Thr Asn His Thr Leu Asn Asn Leu Val Glu
65                  70                  75                  80

Lys Leu Leu Arg Glu Glu Ala Glu Gly Ala Arg Trp Thr Ser Tyr Arg
                85                  90                  95

Phe Ser Arg Val Cys Arg Leu His Arg Gly Gln Leu Ser Leu Phe Cys
            100                 105                 110

Leu Glu Asp Lys Glu Leu Leu Cys Cys Ser Cys Gln Ala Asp Pro Arg
        115                 120                 125

His Gln Gly His Arg Val Gln Pro Val Lys Asp Thr Ala His Asp Phe
    130                 135                 140

Arg Ala Lys Cys Arg Asn Met Glu His Ala Leu Arg Glu Lys Ala Lys
145                 150                 155                 160

Ala Phe Trp Ala Met Arg Ser Tyr Glu Ala Ile Ala Lys His Asn
                165                 170                 175

Gln Val Glu Ala Ala Trp Leu Glu Gly Arg Ile Arg Gln Glu Phe Asp
            180                 185                 190

Lys Leu Arg Glu Phe Leu Arg Val Glu Glu Gln Ala Ile Leu Asp Ala
        195                 200                 205

Met Ala Glu Glu Thr Arg Gln Lys Gln Leu Leu Ala Asp Glu Lys Met
    210                 215                 220
```

```
Lys Gln Leu Thr Glu Thr Glu Val Leu Ala His Glu Ile Glu Arg
225                 230                 235                 240

Leu Gln Met Glu Met Lys Glu Asp Asp Val Ser Phe Leu Met Lys His
            245                 250                 255

Lys Ser Arg Lys Arg Arg Leu Phe Cys Thr Met Glu Pro Glu Pro Val
        260                 265                 270

Gln Pro Gly Met Leu Ile Asp Val Cys Lys Tyr Leu Gly Ser Leu Gln
    275                 280                 285

Tyr Arg Val Trp Lys Lys Met Leu Ala Ser Val Glu Ser Val Pro Phe
290                 295                 300

Ser Phe Asp Pro Asn Thr Ala Ala Gly Trp Leu Ser Val Ser Asp Asp
305                 310                 315                 320

Leu Thr Ser Val Thr Asn His Gly Tyr Arg Val Gln Val Glu Asn Pro
                325                 330                 335

Glu Arg Phe Ser Ser Ala Pro Cys Leu Leu Gly Ser Arg Val Phe Ser
            340                 345                 350

Gln Gly Ser His Ala Trp Glu Val Ala Leu Gly Leu Gln Ser Trp
        355                 360                 365

Arg Val Gly Val Val Arg Val Arg Gln Asp Ser Gly Ala Glu Gly His
370                 375                 380

Ser His Ser Cys Tyr His Asp Thr Arg Ser Gly Phe Trp Tyr Val Cys
385                 390                 395                 400

Arg Thr Gln Gly Val Glu Gly Asp His Cys Val Thr Ser Asp Pro Ala
                405                 410                 415

Thr Ser Pro Leu Val Leu Ala Ile Pro Arg Arg Leu Arg Val Glu Leu
            420                 425                 430

Glu Cys Glu Glu Gly Glu Leu Ser Phe Tyr Asp Ala Glu Arg His Cys
        435                 440                 445

His Leu Tyr Thr Phe His Ala Arg Phe Gly Glu Val Arg Pro Tyr Phe
    450                 455                 460

Tyr Leu Gly Gly Ala Arg Gly Ala Gly Pro Pro Glu Pro Leu Arg Ile
465                 470                 475                 480

Cys Pro Leu His Ile Ser Val Lys Glu Glu Leu Asp Gly
                485                 490
```

<210> SEQ ID NO 5
<211> LENGTH: 4339
<212> TYPE: DNA
<213> ORGANISM: Homo sapiens

<400> SEQUENCE: 5

```
ctcgggtcgc gggcgttggc agccgggcgg gtgggagggg ccggagcaaa agttccgggc      60
gcccgagccg gctgctcgtg ccatggagcg gagtccgac gtgtccccg ggccttcccg       120 ctccttcaag gaggagttgc tctgcgccgt ctgctacgac cccttccgcg acgcagtcac     180
tctgcgctgc ggccacaact tctgccgcgg gtgcgtgagc cgctgctggg aggtgcaggt     240
gtcgcccacc tgcccagtgt gcaaagaccg cgcgtcaccc gccgacctgc gcaccaacca    300
caccctcaac aacctggtgg agaagctgct gcgcgaggag gccgagggcg cgcgctggac    360
cagctaccgc ttctcgcgtg tctgccgcct gcaccgcgga cagctcagcc tcttctgcct   420
cgaggacaag gagctgctgt gctgctcctg ccaggccgac ccccgacacc aggggcaccg   480
cgtgcagccg gtgaaggaca ctgcccacga ctttcgggtg aggagcctga tagccgaaga   540
gagaaggaac ttttttaccaa ctcaccagtg gatagtgaca aagacaaggc tccaaaccag  600
```

-continued

```
ctctcctaac cttcagtcca ggaggcaagg ccaagtgcag gaacatggag catgcactgc    660
gggagaaggc caaggccttc tgggccatgc ggcgctccta tgaggccatc gccaagcaca    720
atcaggtgga ggctgcatgg ctggaaggcc ggatccggca ggagtttgat aagcttcgcg    780
agttcttgag agtggaggag caggccattc tggatgccat ggccgaggag acaaggcaga    840
agcaacttct ggccgacgag aagatgaagc agctcacaga ggagacggag gtgctggcac    900
atgagatcga gcggctgcag atggagatga aggaggacga cgtttctttt ctcatgaaac    960
acaagagccg aaaacgccga ctcttctgca ccatggagcc agagccagtc cagcccggca    1020
tgcttatcga tgtctgcaag tacctgggct ccctgcagta ccgcgtctgg aagaagatgc    1080
ttgcatctgt ggaatctgta cccttcagct ttgaccccaa caccgcagct ggctggctct    1140
ccgtgtctga cgacctcacc agcgtcacca accatggcta ccgcgtgcag gtggagaacc    1200
cggaacgctt ctcctcggcg ccctgcctgc tgggctcccg tgtcttctca cagggctcgc    1260
acgcctggga ggtggccctt gggggctgc agagctggag ggtgggcgtg gtacgtgtgc    1320
gccaggactc gggcgctgag ggccactcac acagctgcta ccacgacaca cgctcgggct    1380
tctggtatgt ctgccgcacg cagggcgtgg agggggacca ctgcgtgacc tcggacccag    1440
ccacgtcgcc cctggtcctg gccatcccac gccgcctgcg tgtggagctg gagtgtgagg    1500
agggcgagct gtctttctat gacgcggagc gccactgcca cctgtacacc ttccacgccc    1560
gctttgggga ggttcgcccc tacttctacc tgggggtgc acgggcgcc gggcctccag    1620 agcctttgcg catctgcccc ttgcacatca gtgtcaagga agaactggat ggctgagctg    1680
gccgggggct gccccggtct tgtgccacag cactgttttc tttctgccct cttcctaatg    1740
cccacactgc ttgggcacta ttgcgcccct gcctccttgc caggctcttc ctcctgtcct    1800
gcctggtcct tttccatgac tccaggctgt gcctctctcc atgtttggtc ccttctgtgc    1860
ccatggtcag gagctattcg ggtggcacct cgctggccag gctctcccga gtcgtggcac    1920
ctccacaatg tgaattttct gaatcccat tccaggattt ctgggaataa tgtttacttc    1980
tagaatgggc ctgttgtaaa ccatctcatc gaggtgtggt aaagccattg gatgaggagg    2040
ggactgccat ggaaaggaga gtttgttact tacggttctg agaggagggg ccacatagga    2100
aagccccacg gtgggtcaga aggcggaagg agggagggga acgtgtgggc aagagacttc    2160
ctctggtttc ctcaggagga aatgggcaag gcagagtaag caggggagac aggtttaagg    2220
gtagctggct tgagtaattt cagtggctct caggataggg gctgcccttt tgtctgata    2280 cctggccccg ggatagtcag gacaggtgaa tgttggcctg gggtgtgaca gccctgggag    2340
agccatgtga aggaggcagc tggcgccatc gctccggatt agttggtttc cataggaaag    2400
gcatgctttc agccagatgc ttgccatctc tagggattgg gggattggct agcctgggag    2460
gatcagtctg tccaggtcag cgaggcccca gataccagag catcaagagt acaggaaata    2520
cagttaatgc agggcctctg tgtggctgga tcctccgtct ccatcagatc agctctgatt    2580
gatctattct tgcacgattt cctctgaaca cagggttcca gagtacttaa acacaacatt    2640 tttaaatcg tgatttcggc ctatttcctt gccaggcctg tttccccacc aggaaatgag    2700
ataggaggac tggatgagga tgtcctgtta tagttgctgt ggaggaagtt cctctggtta    2760
attctcatca gcgtctgcag aaaagaagga aagagggcac cctttcagt tgggaagaaa    2820 ggagaggggt ggcgccatgg acgtggccct aaacgctgtg ggagagggaa gaggaggctg    2880
ggcctcgctg ccctcttgtc tctgctgact tcagcctggt catgcttgct ctgccacttg    2940
cgatttcatc cctaatttct tcctccacca tgcctgcaga cttttccctg ggcttgtttt    3000
```

```
ttctcgcaca tctctgaaga gttttaatc ttcagctcat catgtcccag gaagtggcat    3060
cataaaagga aatatttttt tttcctagga gcagtgttaa atctgggtc acattcctga    3120
ccaaggacag catcctgcct tttggccatc cccttcagtt cacaaaagct gacattttaa    3180
acaaatcatg actcacacgt attaattggt tataaatatg ttgtgtacac tggttagata    3240
aaacttaagg ccacaaggag ggcccaggta ggcgatgtca gtgtgtgaag gggctggatt    3300
gggcgtggtg aggatgttgg caaaccagtg catgcacctg gttggaagat gctcagcctc    3360
acaaaagctc caagccctt gggagccaaa gtgtctgaga gtgtgaccct ctcctgtaaa    3420
gtatttatcc cacccattaa tataatttct gtataataaa cttgacctga aattatttca    3480
ttctttatat taaacttta aaaatgtttt ttattttcac cttagatatg gaagagttt     3540
tttttttttt tttttttta acaggataac ttgagcaggc taggcctctt aaaaaaaaat    3600
ttgagctaaa actcattttt cttttggcat tttcttttca atgttcttat aagcaaagtt    3660
catccatgtt gtagcatgtg ttcaaccttta ttttttcatc gggtaatatt ccattgtatg    3720
gaatggtagt actacatttt atttatcatg catcgattgg tggacatttg gatcgtttct    3780
acttcttgac tattatacat aatgctgcta ggaactttg tgtatgagtt tttgtgtgga     3840
catatgtttt catttctctt tggtatatgc ctgggagcag atttgctgga tcatatgaaa    3900
ctctatttaa cccttgaggg actcccaaac tgttttccaa tgtggtgaca caattttata    3960
tcccatcaac agggcatgag ggttctgatg actccacatc cctcagtgct tttattatc     4020
tatcttttaa cttagccatc ctagtagggg taatgtggca tctcattgtg attttggttt    4080
gcatttccct gatggcgaat gatattgagc atcttttcat gagcttattg gccatttgca    4140
tatcttctta ggacagctat ctttagatca cttgctcatt ttttaattgg gttatttgtc    4200
tttttattat tgagttgtaa gagtcctttt atagcctggc acaagtccct ttaactggta    4260
tatgattata aaattttct ccgtgagctg tttcatttcc ttgatgatgt cctttgaaat     4320
actaaagctt ttaattttg                                                4339
```

<210> SEQ ID NO 6
<211> LENGTH: 206
<212> TYPE: PRT
<213> ORGANISM: Homo sapiens

<400> SEQUENCE: 6

```
Met Glu Arg Ser Pro Asp Val Ser Pro Gly Pro Ser Arg Ser Phe Lys
 1               5                  10                  15
Glu Glu Leu Leu Cys Ala Val Cys Tyr Asp Pro Phe Arg Asp Ala Val
                20                  25                  30
Thr Leu Arg Cys Gly His Asn Phe Cys Arg Gly Cys Val Ser Arg Cys
            35                  40                  45
Trp Glu Val Gln Val Ser Pro Thr Cys Pro Val Cys Lys Asp Arg Ala
        50                  55                  60
Ser Pro Ala Asp Leu Arg Thr Asn His Thr Leu Asn Asn Leu Val Glu
 65                  70                  75                  80
Lys Leu Leu Arg Glu Glu Ala Glu Gly Ala Arg Trp Thr Ser Tyr Arg
                85                  90                  95
Phe Ser Arg Val Cys Arg Leu His Arg Gly Gln Leu Ser Leu Phe Cys
                100                 105                 110
Leu Glu Asp Lys Glu Leu Leu Cys Cys Ser Cys Gln Ala Asp Pro Arg
            115                 120                 125
```

His Gln Gly His Arg Val Gln Pro Val Lys Asp Thr Ala His Asp Phe
         130                 135                 140

Arg Val Arg Ser Leu Ile Ala Glu Glu Arg Arg Asn Phe Leu Pro Thr
145                 150                 155                 160

His Gln Trp Ile Val Thr Lys Thr Arg Leu Gln Thr Ser Ser Pro Asn
                165                 170                 175

Leu Gln Ser Arg Arg Gln Gly Gln Val Gln Glu His Gly Ala Cys Thr
            180                 185                 190

Ala Gly Glu Gly Gln Gly Leu Leu Gly His Ala Ala Leu Leu
        195                 200                 205

<210> SEQ ID NO 7
<211> LENGTH: 192
<212> TYPE: PRT
<213> ORGANISM: Mus musculus

<400> SEQUENCE: 7

Met Glu Pro Gly Pro Ser Val Ser Pro Gly Pro Ser Arg Ser Phe Lys
1               5                   10                  15

Glu Glu Leu Leu Cys Ala Val Cys Tyr Asp Pro Phe Arg Asp Ala Val
                20                  25                  30

Thr Leu Arg Cys Gly His Asn Phe Cys Arg Arg Cys Val Ser Gly Cys
            35                  40                  45

Trp Glu Val Gln Thr Thr Pro Ser Cys Pro Val Cys Lys Glu Arg Ala
50                  55                  60

Val Pro Gly Glu Leu Arg Thr Asn His Thr Leu Asn Asn Leu Val Glu
65                  70                  75                  80

Thr Leu Leu Arg Glu Glu Ala Glu Gly Ala Arg Trp Thr Gly Arg Arg
                85                  90                  95

Ser Pro Arg Pro Cys Arg Ala His Arg Ala Pro Leu Thr Leu Phe Cys
            100                 105                 110

Leu Glu Asp Lys Glu Leu Leu Cys Cys Ala Cys Gln Ala Asp Ala Arg
        115                 120                 125

His Gln Glu His Arg Val Gln Pro Ile Lys Asp Thr Ala Gln Asp Phe
    130                 135                 140

Arg Ala Lys Cys Lys Asn Met Glu His Val Leu Arg Glu Lys Ala Lys
145                 150                 155                 160

Ala Phe Trp Ala Leu Arg Arg Thr Tyr Glu Ala Ile Ala Lys His Asn
                165                 170                 175

Glu Val Gln Thr Thr Trp Leu Gly Arg Ile Arg Asp Glu Phe Asp
            180                 185                 190

<210> SEQ ID NO 8
<211> LENGTH: 309
<212> TYPE: PRT
<213> ORGANISM: Mus musculus

<400> SEQUENCE: 8

Lys Leu Arg Asp Phe Leu Arg Val Glu Glu Gln Ala Thr Leu Asp Ala
1               5                   10                  15

Met Lys Glu Glu Ser Arg Lys Lys His Leu Gln Ala Glu Glu Lys Met
                20                  25                  30

Lys Gln Leu Ala Glu Gln Thr Glu Ala Leu Ala Arg Glu Ile Glu Arg
            35                  40                  45

Leu Gln Met Glu Met Lys Glu Asp Asp Met Thr Phe Leu Met Lys His
        50                  55                  60

```
Lys Ser Arg Lys Arg Arg Leu Phe Cys Thr Val Glu Pro Ala Pro Leu
 65                  70                  75                  80

Gln Pro Gly Leu Leu Met Asp Ala Cys Lys Tyr Leu Glu Ser Leu Gln
                 85                  90                  95

Tyr Arg Val Trp Lys Lys Met Leu Gly Ser Val Glu Ser Val Pro Phe
            100                 105                 110

Ser Leu Asp Pro Asn Thr Ala Ala Gly Trp Leu Lys Val Ala Asp Asp
        115                 120                 125

Leu Thr Ser Val Ile Asn His Gly Tyr Arg Val Gln Val Glu Asn Pro
130                 135                 140

Glu Arg Phe Ser Ser Ala Pro Cys Leu Leu Gly Ser Gln Val Phe Ser
145                 150                 155                 160

Lys Gly Ser His Ser Trp Glu Val Asp Val Gly Gly Leu Pro Thr Trp
                165                 170                 175

Arg Val Gly Val Val Arg Val Gln Ala His Ala Gln Ala Gln Ala Gln
            180                 185                 190

Ala Asp Val Gly Gly Glu Gly His Ser His Ser Cys Tyr His Asp Thr
        195                 200                 205

Arg Ser Gly Phe Trp Tyr Leu Cys Arg Thr Gln Gly Val Asp Gly Asp
210                 215                 220

His Cys Met Thr Ser Asp Thr Ala Thr Ala Pro Leu Val Gln Ala Met
225                 230                 235                 240

Pro Arg Arg Leu Arg Val Glu Leu Glu Cys Glu Gly Glu Leu Ser
                245                 250                 255

Phe Tyr Asp Ser Glu Arg His Cys His Leu Tyr Thr Phe His Ala His
            260                 265                 270

Phe Gly Glu Val Arg Pro Tyr Phe Tyr Leu Gly Ala Ser Arg Gly Asp
        275                 280                 285

Gly Pro Pro Glu Pro Leu Arg Ile Cys His Leu Arg Val Ser Ile Lys
290                 295                 300

Glu Glu Leu Asp Ile
305

<210> SEQ ID NO 9
<211> LENGTH: 21
<212> TYPE: DNA
<213> ORGANISM: Mus musculus

<400> SEQUENCE: 9
acaaggagcu gcugugcugu u                                           21

<210> SEQ ID NO 10
<211> LENGTH: 16
<212> TYPE: PRT
<213> ORGANISM: Mus musculus

<400> SEQUENCE: 10

Phe Lys Glu Glu Leu Leu Cys Ala Val Cys Tyr Asp Pro Phe Arg Asp
  1               5                  10                  15

<210> SEQ ID NO 11
<211> LENGTH: 48
<212> TYPE: DNA
<213> ORGANISM: Mus musculus

<400> SEQUENCE: 11
ttcaaagagg agctgctgtg tgccgtgtgc tacgacccgt tccgcgac              48
```

```
<210> SEQ ID NO 12
<211> LENGTH: 48
<212> TYPE: DNA
<213> ORGANISM: Mus musculus

<400> SEQUENCE: 12
ttcaaagagg agctgctgtt agccgtgggc tacgacccgt tccgcgac          48

<210> SEQ ID NO 13
<211> LENGTH: 48
<212> TYPE: DNA
<213> ORGANISM: Mus musculus

<400> SEQUENCE: 13
aagtttctcc tcgacgacaa tcggcacccg atgctgggca aggcgctg          48

<210> SEQ ID NO 14
<211> LENGTH: 39
<212> TYPE: DNA
<213> ORGANISM: Mus musculus

<400> SEQUENCE: 14
gaggagctgc tgttagccgt gggctacgac ccgttccgc                    39

<210> SEQ ID NO 15
<211> LENGTH: 39
<212> TYPE: DNA
<213> ORGANISM: Mus musculus

<400> SEQUENCE: 15
gcggaacggg tcgtagccca cggctaacag cagctcctc                    39
```

TRANSCRIPTION FACTOR MODULATOR

PRIORITY CLAIM

This application is a continuation of U.S. patent application Ser. No. 12/296,256, filed Dec. 15, 2008 now abandoned, which is the U.S. national stage of International Patent Application No. PCT/AU2007/000459, filed Apr. 5, 2007, which claims priority to and the benefit of Australian Patent Application No. 2006901820, filed Apr. 7, 2006, and Australian Patent Application No. 2006901818, filed Apr. 7, 2006, the contents of each of which are incorporated by reference herein.

FIELD

The present invention relates to novel agents that are useful for modulating transcription factor activity. In particular, the present invention relates to a transcription factor modulator that is capable of affecting ubiquitination, sumoylation and PIAS proteins and thereby modulation of the PIAS-regulated gene expression by STATs, p53, and other transcription factors.

BACKGROUND

Disregulation of the immune system is involved in numerous pathologies, and may be a factor that favours the establishment, maintenance or progression of disease. Deficient immune responses or immune suppression are known to enhance an animal's susceptibility to infection or to the development of cancer. Conversely, excessive or inappropriate immune responses are involved in the establishment or progression of unwanted inflammation or autoimmune conditions. It would thus be advantageous to be able to utilize agents that modulate immune responses, and to at least partially reverse-immune dysfunction when such dysfunction is a component of a given pathological condition.

The tumor suppressor protein p53 functions as a transcriptional factor that activates genes controlling cell cycle arrest and apoptosis (see, for example, Agarwal et al., 1998, *J Biol Chem*, 273(1): p1-4; Lakin & Jackson, 1999, *Oncogene*, 18(53): p7644-55; Sionov & Haupt, 1999, *Oncogene*, 18(45): p6145-6157). The activity of the p53 tumor suppressor protein and the c-Jun proto-oncogene are regulated by posttranslational modifications, such as phosphorylation or ubiquitination (Meek, 1999, *Oncogene*, 18(53): p7666-75). Specifically, covalent attachment of the ubiquitin-like modifier SUMO appears to modulate their transcriptional activity Rodriguez et al., 1999, *Embo J*, 18(22): p6455-61; Muller et al., 2000, *J Biol Chem*, 275(18): p13321-9).

Sumoylation proceeds via an enzymatic pathway that is mechanistically analogous to ubiquitination, but requires a different E1-activating enzyme and Ubc9, a SUMO-specific E2-conjugating enzyme (Lin et al., 2004, *FEBS Lett*, 573(1-3): p15-8). PIAS1 act as specific E3-like ligase that promotes sumoylation of p53 and c-Jun in vitro and in vivo. The PTAS proteins physically interact with both p53 and c-Jun and PIAS1 interacts with the tetramerization and C-terminal regulatory domains of p53 in yeast two-hybrid analyses (Megidish et al., 2002, *J Biol Chem*, 277(10): p8255-9). In addition, they bind to Ubc9, suggesting that they recruit the E2 enzyme to their respective substrate. The SUMO ligase activity requires the conserved zinc-finger domain, which is distantly related to the essential RING-finger motif, found in a subset of ubiquitin ligases.

PIAS proteins strongly repress the transcriptional activity of p53, suggesting that the PIAS-SUMO pathway plays a crucial role in the regulation of p53 and other transcription factors (Schmidt & Muller, 2002, *Proc Natl Acad Sci USA*, 99(5): p2872-7).

The STAT-1 transcription factor has been implicated as a tumor suppressor by virtue of its ability to inhibit cell growth and promotion of apoptosis. STAT-1 is required for optimal DNA damage-induced apoptosis. The basal level of the p53 inhibitor Mdm2 is increased in STAT-1(−/−) cells, suggesting that STAT-1 is a negative regulator of Mdm2 expression. STAT-1 interacts directly with p53, an association, which is enhanced following DNA damage. Therefore, in addition to negatively regulating Mdm2, STAT-1 also acts as a co-activator for p53. Hence STAT-1 is another member of a growing family of protein partners able to modulate the p53-activated apoptotic pathway (Townsend et al., 2004, *J Biol Chem*, 279 (7): p5811-20).

Signal transducer and activator of transcription 1 (STAT1) mediates gene expression in response to cytokines and growth factors. Activation of STAT1 is achieved through its tyrosine phosphorylation, a process that involves Jak tyrosine kinases. One of these cytokines, IFN-gamma, induces STAT1 phosphorylation and leads to expression of multiple genes and apoptosis.

Viruses can evade the host immune system by inactivating different components of the IFN-activated JAK-STAT pathway. As described earlier, members of the Paramyxovirus family of RNA viruses target STATs for degradation. Epstein-Barr virus (EBV) inhibits the expression of IFN-receptor through the action of the EBV immediate-early protein, BZLF1 (Morrison et al., 2001, *Immunity*, 15(5): p787-99). Human cytomegalovirus inhibits IFN-induced expression of MHC class II molecules by selectively targeting JAK1 for degradation (Miller et al., 1998, *J Exp Med*, 187(5): p675-83). By contrast, infection with varicella-zoster virus inhibits the expression of STAT1 and JAK2, but not JAK1 (Abendroth et al., 2000, *J Virol*, 74(4): p1900-7). Individuals with defects in the IFN-JAK-STAT pathway show increased susceptibility to viruses and intracellular bacteria. Patients with mutations in the IFN-receptor chains are susceptible to infection with mycobacteria (Dupuis et al., 2000, *Immunol Rev*, 178: p129-37). Recently, patients with STAT1 deficiency have been reported (Dupuis et al., 2003, *NatGenet*, 33(3): p388-91). These individuals suffered from mycobacterial infection and died of lethal viral disease.

The aetiopathology of Crohn's disease—a chronic inflammatory bowel disease—is poorly understood. Mice with tissue-specific disruption of Stat3 during haematopoiesis show Crohn's disease-like pathogenesis (Welte et al., 2003, *Proc Natl Acad Sci USA*, 100(4): p1879-84). In addition, constitutively tyrosine phosphorylated STAT3 is found in intestinal T cells from patients with Crohn's disease (Lovato et al., 2003, *J Biol Chem*, 278(19): p16777-81). These results indicate that the dysregulation of STAT3 signaling might be involved in the pathogenesis of Crohn's disease. However, the exact role of STAT3 in the pathogenesis of Crohn's disease is not understood.

Apart from its affect on the JAK/STAT pathway, PIAS1 has been shown to be a negative regulator of the NF-KB signaling (Liu et al., 2005, *Mol Cell Biol*, 25(3): p1113-23). The NF-KB family of transcription factors is activated by a wide variety of signals to regulate a spectrum of cellular processes. The proper regulation of NF-KB activity is critical, since abnormal NF-KB signaling is associated with a number of human illnesses, such as chronic inflammatory diseases and cancer. Upon cytokine stimulation, the p65 subunit of NF-KB translocates into the nucleus, where it interacts with PIAS1. The binding of PIAS1 to p65 inhibits cytokine-induced NF-KB-dependent gene activation. PIAS1 blocks the DNA binding activity of p65 both in vitro and in vivo.

The ubiquitin-proteolysis system, which was discovered a little over 20 years ago by Hershko and Ciechanover, was originally thought to eliminate "old", damaged, misfolded or misassembled proteins (Hershko & Ciechanover, 1998, *Annu Rev Biochem*, 67: p425-79; Hershko et al., 2000, *Nat Med*, 6(10): p1073-81). The system acquired its name from a 76-amino acid (aa) ubiquitously expressed protein, which is highly conserved in all eukaryotes. The ubiquitin pathway consists of several components that act sequentially in a hierarchical mode: a concerted two-step reaction that results in a high-energy thioester linkage between ubiquitin and a single conserved ubiquitin-activating enzyme (E1) and ubiquitin transfer through trans-acylation to one of several ubiquitin-conjugating enzymes (Ubcs or E2s). The latter collaborate with a large series of E3s (protein-ubiquitin ligases) in attaching ubiquitin molecules to the ε-amino group of the substrate's lysine residues, thus creating a reversible isopeptide bond. Pathways critical to cancer and immune regulation are regulated at several steps by polyubiquitination (Hershko & Ciechanover, 1998, supra; Ciechanover et al., 2000, *J Cell Biochem Suppl*, 34: p40-51; Schwartz & Hochstrasser, 2003, *Trends Biochem Sci*, 28(6): p321-8; Ben-Neriah, 2002, *Nat Immunol*, 3(1): p20-6).

Recent focus on the system has emphasized its role in controlling cellular processes via two modes of action. These are proteolysis-associated polyubiquitination for controlling the abundance of regulatory proteins and proteolysis-independent ubiquitination: mono-, multi- or polyubiquitination of regulatory proteins (Ciechanover et al., 2000, *Bioessays*, 22(5): p442-51). When the ubiquitins are linked to each other through the lysine amino acid found at position 48 of each ubiquitin, the target protein is directed to the cellular waste-disposal unit, the proteasome (Amit & Ben-Neriah, 2003, *Semin Cancer Biol*, 13(1):p15-28). If lysine 63 is used instead, it can serve as a signal for the target to assemble with other proteins (Wang et al., 2001, *Nature*, 412(6844): p346-51; Deng et al., 2000, *Cell*, 103(2): p351-61).

For proteolysis-associated ubiquitination, a further, poorly characterized, catalytic step is required: polymerization of a ubiquitin chain, which is facilitated by the same E2-E3 pair that attached the first ubiquitin molecule to the substrate or by additional enzymatic components. The polyubiquitin chain then serves as a recognition marker for the substrate-degrading 26S protein complex, the proteasome.

Parallel to the "classical" ubiquitination systems, there are other related enzymatic pathways that covalently attach ubiquitin-like molecules (Ubls) to target proteins for diverse purposes (Hochstrasser, 2000, *Nat Cell Biol*, 2(8): pE153-7; Jentsch & Pyrowolakis, 2000, *Trends Cell Biol*, 10(8): p335-42). Ubls are not only structurally related to ubiquitin, but conjugate to their protein targets through a ubiquitination-like enzymatic process, that is, formation of an isopeptide bond between the Ubl COOH-terminal glycine and an amino group of a target protein lysine. In addition, Ubl conjugation is done by enzymes that are related to ubiquitin pathway E1 and E2s (Hochstrasser, 2000, supra; Jentsch & Pyrowolakis, 2000, supra). Certain Ubl modifications may support protein ubiquitination: an example is the attachment of the Nedd8 Ubl to a subunit of the IB E3 protein that results in enhanced IB ubiquitination (Read et al., 2000, *Mol Cell Biol*, 20(7): p2326-33; Kawakami et al., 2001, *Embo J*, 20(15): p4003-12). Other Ubl modifications may interfere with protein ubiquitination, for example, the attachment of SUMO (small ubiquitin modifier) Ubl to IB, which suppresses its ubiquitination (Hay, 2001, *Trends Biochem Sci*, 26(5): p. 332-3), or have ubiquitination-unrelated functions, such as regulating nuclear protein export (Mahajan et al., 1997, *Cell*, 88(1): p97-107).

Whereas a single E1 activates ubiquitin, many (at least 25 in mammals) E2 species have been characterized in every eukaryotic organism. The multitude of E2 enzymes indicates that they specialize in distinct ubiquitination processes; however, the biochemical basis for this putative specialization is mostly unknown. Whereas E2 proteins are identified by their homology, the E3s constitute a highly heterogeneous class of proteins, which nevertheless can be classified into three groups: HECT (homologous to E6-AP COOH-terminus), RING and Ufd2-related (U-box) E3s (Weissman, 2001, *Nat Rev Mol Cell Biol*, 2(3): p169-78; Jackson et al., 2000, *Trends Cell Biol*, 10(10): p429-39). The HECT E3s are related to E6-associated protein (E6-AP)-the E3 that targets p53 in complex with papillomavirus E6 protein-and share a 350-aa HECT domain. HECT E3s have a unique mode of action: they catalyze ubiquitin transfer to the substrate through an intermediate thiol-ester between ubiquitin and a conserved cysteine in the HECT domain, In contrast, it appears that the RING E3s do not directly participate in the chemical transfer of ubiquitin to the substrate, but merely coordinate the activity of their associated E2s (Meroni & Diez-Roux, 2005, *Bioessays*, 27(11): p1147-57).

RING E3s are distinguished by the metal-coordinated RING-finger motif. The RING E3s are either single proteins with a substrate-targeting motif, such as an SH2 domain, or multi-subunit protein complexes in which substrate-targeting and the RING function are carried out by different proteins. Some of the most remarkable recent advances in the ubiquitin field have been made in characterizing the composition, partial structure and mode of substrate-recognition of three large multisubunit RING E3s: APC/C (anaphase-promoting complex-cyclosome), SCF (Skp1-cullin-1-F-box protein) and VCB (VHL-elongin C-elongin B complex) (Jackson et al., 2000, *Trends Cell Biol*, 10(10): p429-39; Deshaies et al., 1999, *Annu Rev Cell Dev Biol*, 15: p435-67; Zachariae & Nasmyth, 1999, *Genes Dev*, 13(16): p2039-58; Kondo & Kaelin, 2001, *Exp Cell Res*, 264(1): p117-25). U-box E3s constitute a newly identified class, some of which may mediate the assembly of polyubiquitin chains on proteins ubiquitinated by other E3s (Hatakeyama et al., 2001, *J Biol Chem*, 276(35): p33111-20).

Having a fundamental regulatory role in every eukaryotic organism, it is not surprising that proteolysis-associated ubiquitination also fulfills an important role in the immune system. Proteolysis-associated ubiquitination drives a variety of immunity-related regulatory events, from transcriptional activation to apoptosis (Shmueli & Oren, 2005, *Cell*, 121(7): p963-5). Parallel to well established proteolysis-associated ubiquitination, there are important proteosome-mediated degradation events in which the precise role of ubiquitination is still unclear; among the latter, antigen-processing is a prominent example (Kloetzel, 2001, *Nat Rev Mol Cell Biol*, 2(3): p179-87; Yewdell, 2001, *Trends Cell Biol*, 11(7): p294-7).

Ubiquitination of transcription factors can control their activity independently of proteosomal degradation. For example, Met4, a bZIP factor that regulates a large number of genes predominantly involved in methionine biosynthesis, is ubiquitinated but not degraded in the presence of high intracellular levels of S-adenosylmethionine (Kaiser et al., 2000, *Cell*, 102(3): p303-14). Ubiquitination inactivates Met4 at least in part because it precludes recruitment of the coactivator, Cbfl (Kaiser et al., 2000, supra); in addition, binding of Met4 to a subclass of its target promoters is compromised by ubiquitination (Kuras et al., 2002, *Mol Cell*, 10(1): p69-80). Ubiquitination does not necessarily inhibit transcription factors since ubiquitination of the HIVTat protein by Mdm2 augments its ability to activate transcription (Bres et al., 2003, *Nat Cell Biol*, 5(8): p754-61). Similarly, ubiquitination of Myc by Skp2 contributes to transcriptional activation, potentially by allowing Myc to recruit proteasomal subunits that have a proteolysis-independent role in transcriptional activation (Ferdous et al., 2001, *Mol Cell*, 7(5): p981-91). Two signals are known to determine whether ubiquitination leads to degradation. Proteolytic substrates are modified by polyubiquitin chains, and a minimum chain length of about four ubiquitin residues appears to be required to target the attached protein to the proteasome (Flick et al., 2004, *Nat Cell Biol*, 6(7): p634-41). The lysine residue of ubiquitin, used for polyubiquitin chain formation, specifies the second signal. Whereas chains linked through lysine 48 usually lead to proteasomal degradation, those linked through lysine-63 of ubiquitin do not target proteins to the proteasome (Bres et al., 2003, supra).

The TRIM/RBCC proteins are defined by the presence of the tripartite motif composed of a RING domain, one or two B-box motifs and a coiled-coil region (Reymond et al., 2001, *Embo J*, 20(9): p2140-51). These proteins are involved in a plethora of cellular processes such as apoptosis, cell cycle regulation and viral response. Consistently, their alteration results in many diverse pathological conditions. The highly conserved structure of these proteins suggests that a common biochemical function may underlie their assorted cellular roles. Some TRIM/RBCC proteins are implicated in ubiquitination and propose that this large protein family represents a novel class of 'single protein RING finger' ubiquitin E3 ligases (Meroni & Diez-Roux, 2005, supra).

Ubiquitin ligases play a key role in protein localization, transcriptional modulation and protein turnover within the cell. Modulation of these targets presents a novel approach to treating diseases where the normal cell processes are out of balance, such as in cancer where the cell cycling is abnormal. Ubiquitin ligase cancer targets play a role in the regulation of stability, localization, and activity of key proteins such as oncoproteins and tumour suppressor genes. Ubiquitin ligase targets are numerous and modular. This provides the potential for intervening in a highly specific fashion in a disease, potentially improving efficacy and minimizing side-effects.

It can be seen that transcription factors play a major role in homeostasis, especially with respect to the immune system. Accordingly, if modulators or regulators of transcription factors like those discussed above can be identified it might be possible to regulate cell proliferation, migration, and/or differentiation.

SUMMARY

Inventors have shown that HLS5 is a potent activator on the IFN-gamma activation site (GAS)-like elements located upstream of a luciferase reporter. Also HLS5 can be co-immunoprecipitated with PIAS and can induce its degradation. These results demonstrate that by regulating PIAS and ubiquitination, HLS5 modulates gene expression by transcription factors such as STATs.

Accordingly, in a first aspect the present invention provides a transcription factor modulator comprising:
 (i) a pharmaceutically-effective amount of a HLS-5 polypeptide, isoform thereof, functional fragment thereof or pharmaceutical composition thereof; or
 (ii) a compound or composition capable of regulating the endogenous levels of HLS-5 or its activity; or
 (iii) combinations thereof.

In a second aspect the present invention provides a ubiquitin ligase comprising:
 (i) a pharmaceutically-effective amount of a HLS-5 polypeptide, isoform thereof, functional fragment thereof or pharmaceutical composition thereof; or
 (ii) a compound or composition capable of regulating the endogenous levels of HLS-5 or its activity; or
 (iii) combinations thereof.

In some embodiments, the HLS-5 polypeptide will comprise the sequence set out in SEQ ID NO:2, SEQ ID NO:4 or SEQ ID NO:6 or a polypeptide substantially homologous thereto, or a functional fragment thereof.

It is to be clearly understood that the HLS-5 polypeptide of the present invention also includes polypeptide analogues, including but not limited to the following:
1. HLS-5 polypeptide in which one or more amino acids is replaced by its corresponding D-amino acid. The skilled person will be aware that retro-inverso amino acid sequences can be synthesised by standard methods. See for example Chorev and Goodman, 1993, *Acc Chem Res*, 26: 266-273;
2. Peptidomimetic compounds of HLS-5, in which the peptide bond is replaced by a structure more resistant to metabolic degradation. See, for example, Olson et al, 1993, *J. Med. Chem.*, 36, p3039-3049.
3. HLS-5 polypeptide in which individual amino acids are replaced by analogous structures, for example gem-diaminoalkyl groups or alkylmalonyl groups, with or without modified termini or alkyl, acyl or amine substitutions to modify their charge.

The use of such alternative structures can provide significantly longer half-life in the body, since they are more resistant to breakdown under physiological conditions.

Methods for combinatorial synthesis of polypeptide analogues and for screening of polypeptides and polypeptide analogues are well known in the art (see, for example, Gallop et al., 1994, *J. Med. Chem.*, 37, p1233-1251). It is particularly contemplated that the HLS-5 polypeptides of the invention are useful as templates for design and synthesis of compounds of improved activity, stability and bioavailability.

Preferably where amino acid substitution is used, the substitution is conservative, i.e., an amino acid is replaced by one of similar size and with similar charge properties.

In some embodiments, the HLS-5 polypeptide will be expressed in vivo from a vector comprising a polynucleotide encoding HLS-5. In some embodiments, the HLS-5 polynucleotide will be selected from the group consisting of:
 (a) polynucleotides comprising the nucleotide sequence set out in SEQ ID NO:1, SEQ ID NO:3 or SEQ ID NO:5, or a functional fragment thereof;
 (b) polynucleotides comprising a nucleotide sequence capable of hybridizing selectively to the nucleotide sequence set out in SEQ ID NO:1, SEQ ID NO:3 or SEQ ID NO:5, or a functional fragment thereof;
 (c) polynucleotides comprising a polynucleotide sequence which is degenerate as a result of the genetic code to the polynucleotides defined in (a) or (b);
 (d) polynucleotides complementary to the polynucleotides of (a) or (b).

The present invention also provides a vector comprising a HLS-5 polynucleotide of the invention, for example an expression vector comprising a HLS-5 polynucleotide of the invention, operably linked to regulatory sequences capable of directing expression of said polynucleotide in a host cell.

Accordingly, in a third aspect, the present invention provides a transcription factor modulator comprising a vector comprising a HLS-5 polynucleotide of the invention, operably linked to regulatory sequences capable of directing expression of said polynucleotide in a host cell.

In some embodiments, the transcription factor modulator acts as a ubiquitin ligase.

In a fourth aspect the present invention provides a method of modulating transcription factor activity in vivo comprising the step of administering to a subject in need thereof:

(i) a pharmaceutically-effective amount of a HLS-5 polypeptide, isoform thereof, functional fragment thereof or pharmaceutical composition thereof; or (ii) a compound or composition capable of regulating the endogenous levels of HLS-5 or its activity; or (iii) combinations thereof.

In some embodiments, the transcription factor modulator will negatively control transcription factor activity i.e. directly or indirectly prevent transcription factor function and/or reverse transcription factor activity. In yet other embodiments, the transcription factor modulator will positively control transcription factor activity i.e. directly or indirectly bring about or enhance transcription factor activity.

In a fifth aspect the present invention provides a method of modulating transcription factor activity in vitro comprising the step of administering to cells:

(i) a pharmaceutically-effective amount of a HLS-5 polypeptide, isoform thereof, functional fragment thereof or pharmaceutical composition thereof; or (ii) a compound or composition capable of regulating the endogenous levels of HLS-5 or its activity; or (iii) combinations thereof.

In a sixth aspect the present invention provides a method for treating or preventing a condition associated with transcription factor disregulation comprising the step of administering to a subject in need thereof:

(i) a pharmaceutically-effective amount of a HLS-5 polypeptide, isoform thereof, functional fragment thereof or pharmaceutical composition thereof; or (ii) a compound or composition capable of regulating the endogenous levels of HLS-5 or its activity; or (iii) combinations thereof.

In some embodiments the condition will be directly affected by, or controlled by, transcription factors. In other embodiments, the condition will not be directly affected by or controlled by transcription factors; however, the administration of the transcription factor modulator improves, alleviates or treats the condition by controlling the transcription factors associated with or affected by the condition.

The transcription factor modulator of the invention may be administered by any suitable route, and the person skilled in the art will readily be able to determine the most suitable route and dose for the condition to be treated. Dosage will be at the discretion of the attendant physician or veterinarian, and will depend on the nature and state of the condition to be treated, the age and general state of health of the subject to be treated, the route of administration, and any previous treatment which may have been administered.

The transcription factor modulator may be administered in the form of a composition further comprising a pharmaceutically acceptable carrier. This will usually comprise at least one excipient, for example selected from the group consisting of sterile water, sodium phosphate, mannitol, sorbitol, sodium chloride, and any combination thereof.

Methods and pharmaceutical carriers for preparation of pharmaceutical compositions are well known in the art, as set out in textbooks such as Remington's Pharmaceutical Sciences, 20th Edition, Williams & Wilkins, Pennsylvania, USA.

The carrier or diluent, and other excipients, will depend on the route of administration, and again the person skilled in the art will readily be able to determine the most suitable formulation for each particular case.

The subject may be a human, or may be a domestic, companion or zoo animal. While it is particularly contemplated that the transcription factor modulator of the invention is suitable for use in medical treatment of humans, it is also applicable to veterinary treatment, including treatment of companion animals such as dogs and cats, and domestic animals such as horses, cattle and sheep, or zoo animals such as non-human primates, felids, canids, bovids, and ungulates.

DETAILED DESCRIPTION OF THE PREFERRED EMBODIMENTS

Figure 1:
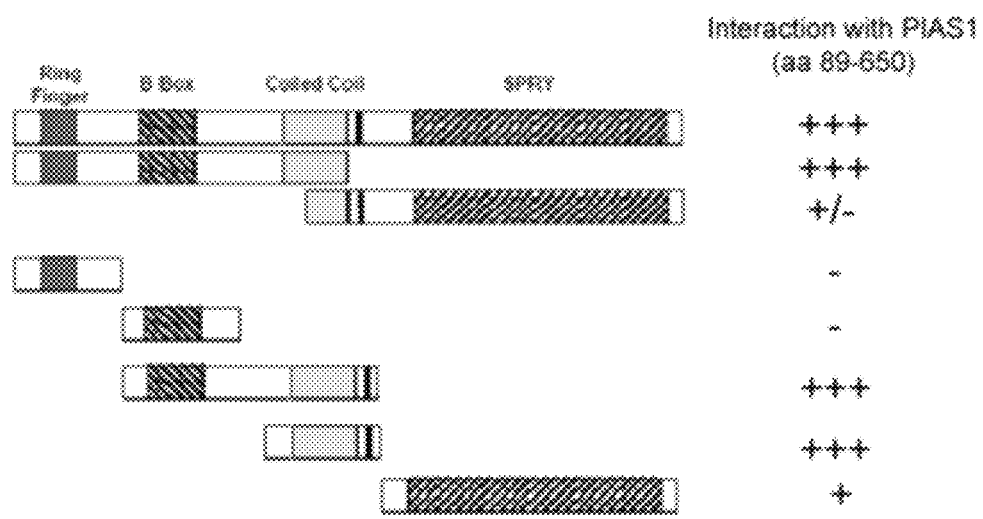
FIG. 1 shows the domain structure of HLS5, and the yeast two-hybrid interaction with PIAS1.

Before describing the present invention in detail, it is to be understood that this invention is not limited to particularly exemplified HLS-5 sequences, expression techniques or methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

The practice of the present invention will employ, unless otherwise indicated, conventional techniques of cell biology, cell culture, molecular biology, recombinant DNA, pharmacology and immunology, which are within the skill of the art. Such techniques are described in the literature. See, for example, Bailey & 011 is, 1986, "Biochemical Engineering Fundamentals", 2nd Ed., McGraw-Hill, Toronto; Coligan et al., 1999, "Current protocols in Protein Science" Volume I and II (John Wiley & Sons Inc.); "DNA Cloning: A Practical Approach", Volumes I and II (Glover ed., 1985); Handbook of Experimental Immunology, Volumes I-IV (Weir & Blackwell, eds., 1986); Immunochemical Methods in Cell and Molecular Biology (Mayer and Walker, eds., Academic Press, London, 1987), Methods in Enzymology, Vols. 154 and 155 (Wu et al. eds. 1987); "Molecular Cloning: A Laboratory Manual", $2^{nd}$ Ed., (ed. by Sambrook, Fritsch and Maniatis) (Cold Spring Harbor Laboratory Press: 1989); "Nucleic Acid Hybridization", (Hames & Higgins eds. 1984); "Oligonucleotide Synthesis" (Gait ed., 1984); Remington's Pharmaceutical Sciences, $17^{th}$ Edition, Mack Publishing Company, Easton, Pa., USA.; "The Merck Index", $12^{th}$ Edition (1996), Therapeutic Category and Biological Activity Index; and "Transcription & Translation", (Hames & Higgins eds. 1984).

It must be noted that as used herein and in the appended claims, the singular forms "a," "an," and "the" include plural reference unless the context clearly dictates otherwise. Thus, for example, a reference to "a nucleic acid molecule" includes a plurality of such molecules, and a reference to "an agent" is a reference to one or more agents, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

The present invention encompasses the following aspects: preparation of a transcription factor modulator of the present invention; preparation of the polynucleotide encoding said HLS-5 polypeptide or a recombinant vector carrying and expressing said polynucleotide; transformants carrying said vector; methods of producing said transformants; methods of detecting the HLS-5 polypeptide; methods of detecting the mRNA or polynucleotide encoding said HLS-5 polypeptide; and methods of treating conditions caused by or exacerbated by unregulated transcription factor activity are explained below.

In the description that follows, if there is no instruction, it will be appreciated that techniques such as gene recombinant techniques, production of recombinant polypeptides in animal cells, insect cells, yeast and *Escherichia coli*, molecular-biological methods, methods of separation and purification of expressed HLS-5 polypeptides, assays and immunological methods, are well-known in this field and any such technique may be adopted.

In its broadest aspect the present invention provides a transcription factor modulator comprising a pharmaceutically-effective amount of a HLS-5, isoform thereof or functional fragment thereof.

The term "transcription factor modulator" as used herein refers to a compound or composition of matter that is capable of affecting directly or indirectly the activity of a transcription factor. As described supra, transcription factors are able to bind to specific sets of short conserved sequences contained in each promoter. Some of these elements and factors are common, and are found in a variety of promoters and used constitutively; others are specific and their use is regulated. In some embodiments, the transcription factors of the present invention are those associated with PIAS1 and in particular, the p53 pathway. Non-limiting examples of possible transcription factors include PIAS1, c-jun, p53, STAT and NF-KB In some embodiments, the transcription factor modulator activity is as a ubiquitin ligase. The term "ubiquitin ligase" as used herein refers to a compound or composition of matter that is capable of affecting directly or indirectly the ubiquitination of proteins. Therefore, as described supra, polypeptides referred to herein as possessing the activity of "ubiquitination", e.g., such as with regard to the activity of a "ubiquitin ligase", are understood to be capable of forming a thiol ester adduct with the C-terminal carboxyl group of ubiquitin and transferring the ubiquitin to an c-amino group in an acceptor protein by formation of an isopeptide bond.

In some embodiments of the present invention the "transcription factor modulator" is HLS-5. HLS-5 is a member of the RING finger B-box Coiled-coil (RBCC) protein family (Lalonde et al., 2004, *J Biol Chem*, 279, 8181-8189). This group of molecules is also referred to as the tripartite motif family (TRIM) of proteins, because of the characteristic domain architecture that is conserved amongst higher eukaryotes (Reymond et al., 2001, *Embo J*, 20, 2140-2151). Sequence analysis of the mouse and human genomes has identified a diverse array of RBCC proteins, many with unknown functions (Reymond et al., 2001, supra). Several RBCC family members, including PML, TIF1α and Rfp, are mutated in human cancer, implicating RBCC proteins as crucial regulators of cell growth and differentiation (de The et al 1991, *Cell*, 66:675-684). HLS-5 maps to chromosome 8p21, a region frequently deleted in a variety of tumours, and enforced expression of the gene in HeLa cells reduced cell growth, clonogenicity and tumorigenicity (Lalonde et al., 2004, supra). Recent studies have demonstrated that some RBCC members regulate the activity, or steady-state levels, of partner proteins by influencing subcellular localization or post-translational modifications (Diamonti et al., 2002, *Proc Natl Acad Sci USA*, 99, 2866-2871; Pearson et al., 2000, *Nature*, 406, 207-210; Urano et al., 2002, *Nature*, 417, 871-875).

HLS-5 was originally identified as a gene markedly up-regulated during an erythroid to myeloid lineage switch of the J2E erythroid cell line (Klinken et al., 1988, *Proc. Natl. Acad. Sci., USA*, 85, 8506-8510; Lalonde et al., 2004, supra). The myeloid variants displayed a monoblastoid morphology, did not respond to erythropoietin (EPO) and had reduced expression of erythroid-specific transcription factors, including GATA-1 and EKLF (Keil et al., 1995, *Cell Growth Differ.*, 6, 439-448; Williams et al., 1999, *Embo J.*, 18, 5559-5566). Significantly, HLS-5 was isolated independently as a gene induced during macrophage colony stimulating factor-initiated maturation of myeloid cells (Kimura et al., 2003, *J. Biol. Chem.*, 278, 25046-25054).

Therefore, in some embodiments of the present invention the "transcription factor modulator" comprises an isolated full-length HLS-5 polypeptide. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, natural amino acids, etc.), polypeptides with substituted linkages as well as other modifications known in the art, both naturally and non-naturally occurring.

Full length HLS-5 polypeptides of the present invention have about 500 amino acids, encode a tumor suppressor factor in an animal, particularly a mammal, and include allelic variants or homologues. Full length HLS-5 polypeptides also typically comprise a Ring finger motif, a B box, a coiled-coil motif and an SPRY motif. HLS-5 polypeptides of the invention also include fragments and derivatives of full length HLS-5 polypeptides, particularly fragments or derivatives having substantially the same biological activity. The polypeptides can be prepared by recombinant or chemical synthetic methods. In some embodiments, the HLS-5 polypeptides include those comprising the amino acid sequence of SEQ ID NO:2, SEQ ID NO:4 or SEQ ID NO:6, or allelic variants or homologues, including fragments, thereof. In further embodiments, the HLS-5 polypeptides consist essentially of amino acids 12 to 504 of the amino acid sequence shown as SEQ ID NO:4 or allelic variants, homologues or fragments, thereof.

In the context of the present invention, a homologous sequence is taken to include an amino acid sequence which is at least 60, 70, 80 or 90% identical, preferably at least 95 or 98% identical at the amino acid level over at least 20, 50, 100, 200, 300 or 400 amino acids with the amino acid sequences set out in SEQ ID NO:2, SEQ ID NO:4, SEQ ID SEQ ID NO:6 or SEQ ID NO:8. In particular, homology should typically be considered with respect to those regions of the sequence known to be essential for the function of the protein rather than non-essential neighbouring sequences. Thus, for example, homology comparisons are preferably made over regions corresponding to the Ring finger, B box, coiled coil and/or SPRY domains of the HLS-5 amino acid sequence set out in SEQ ID NO:2, SEQ ID NO:4 or SEQ ID NO:8. The ring finger corresponds to approximately amino acids 36 to 75 of SEQ ID NO:2. The B box corresponds to approximately amino acids 111 to 152 of SEQ ID NO:2. The coiled coil corresponds to approximately amino acids 219 to 266 of SEQ ID NO:2.

The SPRY domain corresponds to approximately amino acids 368 to 507 of SEQ ID NO:2. In some embodiments, polypeptides of the invention comprise a contiguous sequence having greater than 50, 60 or 70% homology, more preferably greater than 80 or 90% homology, to one or more of amino acids 111 to 152, 219 to 266 or 368 to 507 of SEQ ID NO:2 or the corresponding regions of SEQ ID NO:4 or SEQ ID NO:6.

In some embodiments, polypeptides may alternatively or in addition comprise a contiguous sequence having greater than 80 or 90% homology, to amino acids 36 to 75 of SEQ ID NO:2 or the corresponding region of SEQ ID NO:4 or SEQ ID NO:6. Other polypeptides comprise a contiguous sequence having greater than 40, 50, 60, or 70% homology, more preferably greater than 80 or 90% homology to amino acids 1 to 35, 76 to 110, 153 to 218 and/or 267 to 367 of SEQ ID NO:2 or the corresponding regions of SEQ ID NO:4 or SEQ ID NO:6. Although homology can also be considered in terms of similarity (i.e. amino acid residues having similar chemical properties/functions), in the context of the present invention it is preferred to express homology in terms of sequence identity. The terms "substantial homology" or "substantial identity", when referring to polypeptides, indicate that the polypeptide or protein in question exhibits at least about 70% identity with an entire naturally-occurring protein or a portion thereof, usually at least about 80% identity, and preferably at least about 90 or 95% identity.

Homology comparisons can be conducted by eye, or more usually, with the aid of readily available sequence comparison programs. These commercially available computer programs can calculate percentage homology between two or more sequences.

Percent (%) homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically/such ungapped alignments are performed only over a relative short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible-reflecting higher relatedness between the two compared sequences-will achieve a higher score than one with many gaps. "Affine gap costs" are typically used that charge a relative high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, USA; Devereux et al., 1984, *Nucleic Acids Research*, 12: 387). Examples of other software than can perform sequence comparisons include, but are not limited to, the BLAST package (see, Ausubel et al., supra), FASTA (Atschul et al., 1990, *J. Mol. Biol.*, 403-410) and the GENEWORKS suite of comparison tools. Both BLAST and FASTA are available for offline and online searching (see Ausubel et al., supra, pages 7-58 to 760). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix-the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

HLS-5 polypeptide homologues include those having the amino acid sequences, wherein one or more of the amino acids are substituted with another amino acid which substitutions do not substantially alter the biological activity of the molecule.

An HLS-5 polypeptide homologue according to the invention preferably has 80% or greater amino acid sequence identity to the human HLS-5 polypeptide amino acid sequence set out in SEQ ID NO:4 or SEQ ID NO:6. Examples of HLS-5 polypeptide homologues within the scope of the invention include the amino acid sequence of SEQ ID NO:4 or SEQ ID NO:6 wherein: (a) one or more aspartic acid residues is substituted with glutamic acid; (b) one or more isoleucine residues is substituted with leucine; (c) one or more glycine or valine residues is substituted with alanine; (d) one or more arginine residues is substituted with histidine; or (e) one or more tyrosine or phenylalanine residues is substituted with tryptophan.

"Protein modifications or functional fragments" are also encompassed by the term "transcription factor modulator" when it refers to HLS-5 polypeptides. HLS-5 polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labelling, e.g., with radionucleotides, and various enzymatic modifications, as will be readily appreciated by those well skilled in the art.

A HLS-5 polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids, wherein said "fragment," "portion" or "segment" has substantially similar function to wild type full length HLS-5 polypeptide.

"Substantially similar function" refers to the function of the polypeptide homologue, variant, derivative or fragment of HLS-5 with reference to the wild-type HLS-5 polypeptide. The "fragment," "portion" or "segment" of HLS-5 should retain is ability to control the sumoylation proteins as shown by (Boggio et al., 2004, *Mol Cell,* 16, 549-561). In some embodiments, the "fragment," "portion" or "segment", will comprise one or more domains that have been identified in other proteins as being important with respect to function. For example, the B30.2/SPRY domain and an additional domain in huTRIM5alpha, comprising the amino-terminal RING and B-box components of the TRIM motif, have been shown to be required for N-MLV restriction activity, while the intervening coiled-coil domain is necessary and sufficient for huTRIM5alpha multimerization. Truncated huTRIM5alpha proteins that lack either or both the N-terminal RING/B-Box or the C-terminal 830.2/SPRY domain form heteromultimers with full-length huTRIM5alpha and are dominant inhibitors of its N-MLV restricting activity, suggesting that homomultimerization of intact huTRIM5alpha monomers is necessary for N-MLV restriction. However, localization in large cytoplasmic bodies is not required for inhibition of N-MLV by huTRIM5alpha or for inhibition of HIV-1 by chimeric or rhTRIM5alpha (Yap et al., 2005, *Curr Biol,* 15, 73-78). Geminin is a cellular protein that associates with Cdt1 and inhibits Mcm2-7 loading during S phase. It prevents multiple cycles of replication per cell cycle and prevents episome replication. Geminin forms a parallel coiled-coil homodimer with atypical residues in the dimer interface. Point mutations that disrupt the dimerization abolish interaction with Cdt1 and inhibition of replication. This interaction is essential for replication inhibition (Saxena et al., 2004, *Mol Cell,* 15, 245-258). Therefore, it is highly likely that functional fragments, portions or segments of HLS-5 will have one or more of the regions identified above. Moreover, techniques well known in the art for identifying or testing the activity of these regions can be used to test or identify if the HLS-5 fragment, portion or segment of the present invention is functional.

In addition to the similarity of function, the modified polypeptide may have other useful properties, such as a longer half-life.

In some embodiments, the HLS-5 fragment is an isoform of HLS-5. HLS-5, like other TRIM proteins, are defined by a cluster of three different RBCC or TRIM protein motifs: a RING motif, which is cysteine-rich and binds zinc; one or two so-called B boxes, which also bind zinc; and a coiled-coil domain that is probably involved in the formation of protein complexes. All individual TRIM proteins homo-oligomerization and some might also form alliances with other TRIM proteins (hetero-oligomerization). There are at least 37 TRIM family members in humans (Reymond et al., 2001, *Embo J,* 20, 2140-2151). Many TRIM family members have alternative splicing, with the best characterised members being TRIM39 (PML) (Duprez et al., 1999, *J Cell Sci,* 112, 381-393), TRIM18 (MID1) (Berti et al., 2004, *BMC Cell Biol,* 5, 9), TRIM32 (LGMD-2H) (Schoser. et al., 2005, *Ann Neurol,* 57, 591-595) and TRIMS (Xu et al., 2003, *Exp Cell Res,* 288, 84-93). Each of the various TRIM proteins seems to localize to particular compartments within cells, forming discrete structures to which they entice other proteins, with different isoforms potentially attracting different subsets of proteins and with alternate functions (Reymond et al., 2001, supra). Based upon the foregoing, HLS-5 has at least one isoform.

The HLS-5 isoform shown in SEQ ID NO:6 includes an alternate exon in the coding region which results in a frame shift and an early stop codon, compared to HLS-5 shown in SEQ ID NO:4. SEQ ID NO:6 isoform is shorter and has a distinct C-terminus compared to HLS-5 in SEQ ID NO:4.

In certain embodiments, the HLS-5 transcription factor modulators are peptidyl compounds (including peptidomimetics) of HLS-5 which have been modified such that they resist or are more resistant to proteolytic degradation and the like. These peptidyl compounds might include functional groups, such as in place of the scissile peptide bond, which facilitates inhibition of a serine-, cysteine- or aspartate-type protease, as appropriate. For example, the HLS-5 peptidyl compound can be a peptidyl diketone or a peptidyl keto ester, a peptide haloalkylketone, a peptide sulfonyl fluoride, a peptidyl boronate, a peptide epoxide, a peptidyl diazomethanes, a peptidyl phosphonate, isocoumarins, benzoxazin-4-ones, carbamates, isocyantes, isatoic anhydrides or the like. Such functional groups have been provided in other peptide molecules, and general routes for their synthesis are known. See, for example, Angelastro et al., 1990, *J. Med. Chem.* 33:11-13; Bey et al., EPO 363,284; Bey et al., EPO 364,344; Grubb et al., WO 88/10266; Higuchi et al., EPO 393,457; Ewoldt et al., 1992, *Molecular Immunology,* 29(6):713-721; Hernandez et al., 1992, *Journal of Medicinal Chemistry,* 35(6): 1121-1129;

Vlasak et al., 1989, *J. Virology* 63(5):2056-2062; Hudig et al., 1991, *J. Immunol.*, 147(4):1360-1368; Odake et al., 1991, *Biochemistry*, 30(8):2217-2227; Vijayalakshmi et al., 1991, *Biochemistry*, 30(8):2175-2183; Kam et al., 1990, *Thrombosis & Haemostasis*, 64(1):133-137; Powers et al., 1989, *J. Cell Biochem.*, 39(1):33-46; Powers et al., Proteinase Inhibitors, Barrett et al., Eds., Elsevier, pp. 55-152 (1986); Powers et al., 1990, *Biochemistry*, 29(12):3108-3118; Oweida et al., 1990, *Thrombosis Research*, 58(2):391-397; Hudig et al., 1989, *Molecular Immunology*, 26(8):793-798; Orlowski et al., 1989, *Archives of Biochemistry & Biophysics*, 269(1): 125-136; Zunino et al., 1988, *Biochimica et Biophysica Acta.*, 967(3):331-340; Kam et al., 1988, *Biochemistry*, 27(7):2547-2557; Parkes et al., 1985, *Biochem J.*, 230:509-516; Green et al., 1981, *J. Biol. Chem.*, 256:1923-1928; Angliker et al., 1987, *Biochem. J.*, 241:871-875; Puri et al., 1989, *Arch. Biochem. Biophys.* 27:346-358; Hanada et al., Proteinase Inhibitors: Medical and Biological Aspects, Katunuma et al., Eds., Springer-Verlag pp. 25-36 (1983); Kajiwara et al., 1987, *Biochem. Int.*, 15:935-944; Rao et al., 1987, *Thromb. Res.*, 47:635-637; Tsujinaka et al., 1988, *Biochem. Biophys. Res. Commun.* 153:1201-1208). See also U.S. Pat. Nos. 4,935,493; 5,462,928; 5,543,396; 5,296,604; and 6,201,132.

In other embodiments, the HLS-5 polypeptide is a non-peptidyl compound, e.g., which can be identified by such drug screening assays as described herein. These non-peptidyl compounds can be, merely to illustrate, synthetic organics, natural products, nucleic acids or carbohydrates.

Also included are such peptidomimetics as olefins, phosphonates, aza-amino acid analogs and the like.

Also deemed as equivalents are any HLS-5-based compounds which can be hydrolytically converted into any of the aforementioned HLS-5 compounds including boronic acid esters and halides, and carbonyl equivalents including acetals, hemiacetals, ketals, and hemiketals, and cyclic dipeptide analogs.

The present invention also encompasses pharmaceutically acceptable salts of the HLS-5 compounds include the conventional non-toxic salts or quaternary ammonium salts of the compounds, e.g., from non-toxic organic or inorganic acids. For example, such conventional non-toxic salts include those derived from inorganic acids such as hydrochloride, hydrobromic, sulphuric, sulfonic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

The pharmaceutically acceptable salts of the present invention can be synthesized from the HLS-5 compounds which contain a basic or acid moiety by conventional chemical methods. Generally, the salts are prepared by reacting the free base or acid with stoichiometric amounts or with an excess of the desired salt-forming inorganic or organic acid or base in a suitable solvent.

Contemplated equivalents of the HLS-5 compounds described above include compounds which otherwise correspond thereto, and which have the same general properties thereof (e.g. the ability to control sumoylation), wherein one or more simple variations of substituents are made which do not adversely affect the efficacy of the HLS-5 molecule in use in the contemplated methods. In general, the HLS-5 polypeptides of the present invention may be prepared by the methods described below, or by modifications thereof, using readily available starting materials, reagents and conventional synthesis procedures. In these reactions, it is also possible to make use of variants which are in themselves known, but are not mentioned here.

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-IUB Commission on Biochemical Nomenclature (see *Biochemistry* (1972) 11:1726-1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the α-amino group. The term "amino acid side chain" is that part of an amino acid exclusive of the —CH(NH$_2$)COOH portion, as defined by Kopple, 1966, "Peptides and Amino Acids", WA Benjamin Inc., New York & Amsterdam, pp 2 and 33; examples of such side chains of the common amino acids are —CH$_2$CH$_2$SCH$_3$ (the side chain of methionine), —CH$_2$(CH$_3$)—CH$_2$CH$_3$ (the side chain of isoleucine), —CH$_2$CH(CH$_3$)$_2$ (the side chain of leucine) or H— (the side chain of glycine).

For the most part, the amino acids used in the application of this invention are those naturally occurring amino acids found in proteins, or the naturally occurring anabolic or catabolic products of such amino acids which contain amino and carboxyl groups.

The term "amino acid residue" further includes analogs, derivatives and congeners of any specific amino acid referred to herein, as well as C-terminal or N-terminal protected amino acid derivatives (eg. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate, functional groups). For instance, the HLS-5 polypeptide can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminiopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers.

The phrase "protecting group" as used herein means substituents which protect the reactive functional group from undesirable chemical reactions. Examples of such protecting groups include esters of carboxylic acids and boronic acids, ethers of alcohols and acetals and ketals of aldehydes and ketones. For instance, the phrase "N-terminal protecting group" or "amino-protecting group" as used herein refers to various amino-protecting groups which can be employed to protect the N-terminus of an amino acid or peptide against undesirable reactions during synthetic procedures. Examples of suitable groups include acyl protecting groups such as, to illustrate, formyl, dansyl, acetyl, benzoyl, trifluoroacetyl, succinyl and methoxysuccinyl; aromatic urethane protecting groups as, for example, benzyloxycarbonyl (Cbz); and aliphatic urethane protecting groups such as t-butoxycarbonyl (Boc) or 9-Fluorenylmethoxycarbonyl (FMOC).

Certain polypeptides of the present invention may exist in particular geometric or stereoisomeric forms. The present invention contemplates all such forms, including cis- and trans-isomers, R- and S-enantiomers, diastereomers, (D)-isomers, (L)-isomers, the racemic mixtures thereof, and other mixtures thereof, as, falling within the scope of the invention. Additional asymmetric carbon atoms may be present in a substituent such as an alkyl group. All such isomers, as well as mixtures thereof, are intended to be included in this invention.

The similarity of function (activity) of the modified HLS-5 polypeptide may be substantially the same as the activity of the wild type HLS-5 polypeptide. Alternatively, the similarity of function (activity) of the modified polypeptide may be higher than the activity of the wild-type HLS-5 polypeptide. The function/biological activity of homologues, variant, derivatives or fragments relative to wild type may be determined, for example, by means of biological assays. For example, when administered to HeLa or COS cells, HLS-5 reduces levels of PIAS1, UBC9 and SUMO-1, which results in a reduction of the overall SUMOylation of some protein products and the induction of others. Thus, one in vivo assay involves the testing for HLS-5 modulation of protein SUMOylation by the administration a variant of HeLa or COS cell, i.e. tissue, etc. and determination of whether cells have altered levels of SUMOylation of individual protein products by western analysis. Preferred homologues, variants and fragments are capable of inhibiting SUMOylation by a factor of at least 0.5 relative to full length HLS-5, preferably by a factor of at least 0.9. Another test, based on the interaction of HLS-5 with elements of the SUMOylation machinery is to do in vitro SUMO-1 modification assay. Basically, a reaction mixture of 20 µl containing 1 µg of tagged protein of interest as the substrate as well as 1 µg of E1 (GST-Uba2, His$_6$-Aos1), 2 µg of E2 (Ubc9), and 1 µg of SUMO-1 in a solution comprising 50 mM Tris-HCl (pH 7.5), 50 mM NaCl, 10 mM ATP, 2 mM MgCl$_2$, and 0.1 mM dithiothreitol is incubated for 2 h at 30° C. (see, for example, Hatakeyama et al., 2001, *J Biol Chem*, 276, 33111-33120). This assay can be done in the presence or absence of HLS-5. The reaction is terminated by the addition of SDS sample buffer containing 5% β-mercaptoethanol and heating at 88° C. for 5 min. Samples can then be fractionated by SDS-PAGE on a 12% gel and subjected to immunoblot analysis with mouse monoclonal antibodies to SUMO-1 (2 µg/ml, anti-GMP-1), Myc (1 µg/ml, 9E10), or GST (1 µg/ml), according to the tag used. Immune complexes can be detected with horseradish peroxidase-conjugated rabbit polyclonal antibodies to mouse immunoglobulin. To determine the extent of inhibition of protein substrate, variant or fragment to HLS-5 in an in vitro SUMOylation assay. Preferred homologues, variants and fragments are capable of binding to HLS5 by a factor of at least 0.5 relative to full length HLS-5, preferably by a factor of at least 0.9. Suitable in vitro SUMOylation assays are well known to skilled persons, such as 'SUMOylation' assays where one substrate is added to the components of the SUMOylation machinery and the modified or "SUMOylation" products are quantified or observed.

As described supra, in some embodiments, the transcription factor modulator activity is as a ubiquitin ligase. Accordingly; in some embodiments, the variant or modified ubiquitin ligase can be tested using an in vitro ubiquitination assay. Briefly, logarithmically growing HeLa cells can be collected at a density of $6 \times 10^5$ cells/ml. Cells are arrested in G1 by 48-hour treatment with 70 µM lovastatin as described (O'Connor &. Jackman, 1995, in Cell Cycle-Materials and Methods, M. Pagano, ed., Springer, N.Y., Chap. 6). 1 µl of in vitro translated [$^{35}$S]p27 is incubated at 30° C. for different times (0-75 minutes) in 10 µl of ubiquitination mix containing: 40 mM Tris pH7.6, 5 mM MgCl$_2$, 1 mM DTT, 10% glycerol, 1 µM ubiquitin aldehyde, 1 mg/ml methyl ubiquitin, 10 mM creatine phosphate, 0.1 mg/ml creatine phosphokinase, 0.5 mM ATP, 1 µM okadaic acid, 20-30 µg HeLa cell extract. Ubiquitin aldehyde can be added to the ubiquitination reaction to inhibit the isopeptidases that would remove the chains of ubiquitin from p27. Addition of methyl ubiquitin competes with the ubiquitin present in the cellular extracts and terminates p27 ubiquitin chains. Such chains appear as discrete bands instead of a high molecular smear. These shorter polyubiquitin chains have lower affinity for the proteasome and therefore are more stable. Reactions are terminated with Laemmli sample buffer containing .beta.-mercaptoethanol and the products can be analyzed on protein gels under denaturing conditions.

Polyubiquitinated p27 forms are identified by autoradiography. p27 degradation assay is performed in a similar manner, except that (i) Methylated ubiquitin and ubiquitin aldehyde are omitted; (ii) The concentration of HeLa extract is approximately 7 µg/µl; (iii) Extracts are prepared by hypotonic lysis (Pagano et al., 1995, *Science* 269:682), which preserves proteasome activity better than the nitrogen bomb disruption procedure. In the absence of methyl ubiquitin, p27 degradation activity, instead of p27 ubiquitination activity, can be measured.

The samples are immunoprecipitated with an antibody to p27 followed by a subsequent immunoprecipitation with an anti-ubiquitin antibody and run on an 8% SDS gel. The high molecular species as determined by this assay are ubiquitinated. As a control, a p27 mutant lacking all 13 lysines can be used.

Other methods of testing ubiquitination are described in the examples infra.

The modified polypeptide may be synthesised using conventional techniques, or is encoded by a modified nucleic acid and produced using conventional techniques. The modified nucleic acid is prepared by conventional techniques. A nucleic acid with a function substantially similar to the wild-type HLS-5 gene function produces the modified protein described above.

Besides substantially full-length polypeptides, the present invention provides for biologically active fragments of the polypeptides. Biologically active fragments are those polypeptide fragments retaining transcription modulating activity.

The present invention also provides for fusion polypeptides, comprising HLS-5 polypeptides and fragments. Homologous polypeptides may be fusions between two or more HLS-5 polypeptide sequences or between the sequences of HLS-5 and a related protein. Likewise, heterologous fusions may be constructed which would exhibit a combination of properties or activities of the derivative proteins.

For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β galactosidase, trpE, protein A, β-lactamase, alpha amylase, alcohol dehydrogenase and yeast alpha mating factor.

Fusion proteins will typically be made by either recombinant nucleic acid methods, as described below, or may be chemically synthesized.

"Protein purification" refers to various methods for the isolation of the HLS-5 polypeptides from other biological material, such as from cells transformed with recombinant nucleic acids encoding HLS-5, and are well known in the art. For example, such polypeptides may be purified by immunoaffinity chromatography employing, eg., the antibodies provided by the present invention. Various methods of protein purification are well known in the art.

The terms "isolated", "substantially pure", and "substantially homogeneous" are used interchangeably to describe a HLS-5 polypeptide that has been separated from components that accompany it in its natural state. A monomeric protein is substantially purified when at least about 60 to 75% of a sample exhibits a single polypeptide sequence. A substantially purified protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for application.

A HLS-5 polypeptide is substantially free of naturally associated components when it is separated from the native contaminants that accompany it in its natural state.

Thus, a HLS-5 polypeptide that is chemically synthesised or synthesised in a cellular system different from the cell from which it naturally originates will be substantially free from its naturally associated components. A protein may also be rendered substantially free of naturally associated components by isolation, using protein purification techniques well known in the art.

A HLS-5 polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

In some embodiments of the present invention the terms "HLS-5 protein" or "HLS-5 polypeptide" refers to a protein or polypeptide encoded by a HLS-5 polynucleotide sequence, variants or functional fragments thereof. Also included are HLS-5 polypeptide encoded by DNA that hybridize under high stringency conditions, to HLS-5 encoding polynucleotides and closely related polypeptides retrieved by antisera to the HLS-5 protein(s). Accordingly, in some embodiments, the term "transcription factor modulator" comprises an HLS-5 polynucleotide molecule that encodes an HLS-5 polypeptide, allelic variant, or analog, including functional fragments, thereof.

Preferred polynucleotide molecules according to the invention include the polynucleotide sequences set out in SEQ ID NO:1 and SEQ ID NO:3 or functional fragments thereof.

A polynucleotide is said to "encode" a polypeptide if, in its native state or when manipulated by methods well known to those skilled in the art, it can be transcribed and/or translated to produce the RNA for and/or the polypeptide or a fragment thereof. The anti-sense strand is the complement of such a nucleic acid, and the encoding sequence can be deduced therefrom.

An "isolated" or "substantially pure" nucleic acid (e.g., RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein that has been removed from its naturally occurring environment, and includes recombinant or cloned DNA isolates and chemically synthesized analogs or analogs biologically synthesized by heterologous systems.

"HLS-5 gene sequence," "HLS-5 gene," "HLS-5 nucleic acids" or "HLS-5 polynucleotide" include coding sequences, intervening sequences and regulatory elements controlling transcription and/or translation. The term "HLS-5 gene sequence" is intended to include all allelic variations of the DNA sequence.

These terms, when applied to a nucleic acid, refer to a nucleic acid that encodes a HLS-5 polypeptide, fragment; homologue or variant, including, e.g., protein fusions or deletions. The nucleic acids of the present invention will possess a sequence that is either derived from, or substantially similar to a natural HLS-5 encoding gene or one having substantial homology with a natural HLS-5 encoding gene or a portion thereof. The coding sequence for murine HLS-5 polypeptide is shown in SEQ ID NO:1, with the amino acid sequence shown in SEQ ID NO:2. The coding sequence for human HLS-5 polypeptide is shown in SEQ ID NO:3 and SEQ ID NO:7, with the amino acid sequence shown in SEQ ID NO:4 and SEQ ID NO:8.

A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

Alternatively, substantial homology or (identity) exists when a nucleic acid or fragment thereof will hybridise to another nucleic acid (or a complementary strand thereof) under selective hybridisation conditions, to a strand, or to its complement. Selectivity of hybridisation exists when hybridisation that is substantially more selective than total lack of specificity occurs. Typically, selective hybridisation will occur when there is at least about 55% identity over a stretch of at least about 14 nucleotides, preferably at least about 65%, more preferably at least about 75%, and most preferably at least about 90%. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Thus, polynucleotides of the invention preferably have at least 75%, more preferably at least 85%, more preferably at least 90% homology to the sequences shown in the sequence listings herein. More preferably there is at least 95%, more preferably at least 98%, homology. Nucleotide homology comparisons may be conducted as described below for polypeptides. A preferred sequence comparison program is the GCG Wisconsin Best fit program described below. The default scoring matrix has a match value of 10 for each identical nucleotide and −9 for each mismatch. The default gap creation penalty is −50 and the default gap extension penalty is −3 for each nucleotide.

In the context of the present invention, a homologous sequence is taken to include a nucleotide sequence which is at least 60, 70, 80 or 90% identical, preferably at least 95 or 98% identical at the amino acid level over at least 20, 50, 100, 200, 300, 500 or 1000 nucleotides with the nucleotides sequences set out in SEQ ID NO:1 or SEQ ID NO:3. In particular, homology should typically be considered with respect to those regions of the sequence that encode contiguous amino acid sequences known to be essential for the function of the protein rather than non-essential neighbouring sequences. Thus, for example, homology comparisons are preferably made over regions corresponding to the Ring finger, B box, coiled coil and/or SPRY domains of the HLS-5 amino acid sequence set out in SEQ ID NO:2, SEQ ID NO:4 or SEQ ID NO:8.

Preferred polypeptides of the invention comprise a contiguous sequence having greater than 50, 60 or 70% homology, more preferably greater than 80, 90, 95 or 97% homology, to one or more of the nucleotides sequences of SEQ ID NO:1 which encode amino acids 111 to 152, 219 to 266 or 368 to 507 of SEQ ID NO:2 or the equivalent nucleotide sequences in SEQ ID NO:3.

Preferred polynucleotides may alternatively or in addition comprise a contiguous sequence having greater than 80, 90, 95 or 97% homology to the sequence of SEQ ID NO: 1 that encodes amino acids 36 to 75 of SEQ ID NO:2 or the corresponding nucleotide sequences of SEQ ID NO:3. Other preferred polynucleotides comprise a contiguous sequence having greater than 40, 50, 60, or 70% homology, more preferably greater than 80, 90, 95 or 97% homology to the sequence of SEQ ID NO:1 that encodes amino acids 1 to 35, 76 to 110, 153 to 218 and/or 267 to 367 of SEQ ID NO:2 or the corresponding nucleotide sequences of SEQ ID NO:3.

Nucleotide sequences are preferably at least 15 nucleotides in length, more preferably at least 20, 30, 40, 50, 100 or 200 nucleotides in length.

Generally, the shorter the length of the polynucleotide, the greater the homology required to obtain selective hybridization. Consequently, where a polynucleotide of the invention consists of less than about 30 nucleotides, it is preferred that the % identity is greater than 75%, preferably greater than 90% or 95% compared with the HLS-5 nucleotide sequences set out in the sequence listings herein.

Conversely, where a polynucleotide of the invention consists of, for example, greater than 50 or 100 nucleotides, the % identity compared with the HLS-5 nucleotide sequences set out in the sequence listings herein may be lower, for example greater than 50%, preferably greater than 60 or 75%.

Nucleic acid hybridisation will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. An example of stringent hybridization conditions is 65° C. and 0.1×SSC (1×SSC=0.15M NaCl, 0.015M sodium citrate pH 7.0).

The "polynucleotide" compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.).Also included are synthetic molecules that mimic polynucleotides in their ability to bind to a designated sequence via hydrogen bonding and other chemical interactions.

Such molecules are known in the art and include, for example, those in which peptide linkages substitute for phosphate linkages in the backbone of the molecule. The present invention provides recombinant nucleic acids comprising all or part of the HLS-5 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered, e.g., by deletion, substitution or insertion.

A "recombinant nucleic acid" is a nucleic acid that is not naturally occurring, or which is made by the artificial combination of two otherwise separated segments of sequence. This artificial combination is often accomplished by either chemical syntheses means, or by the artificial manipulation of isolated segments of nucleic acids, by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source that is abundant in'mRNA for the desired proteins. Phage libraries are normally preferred, but other types of libraries may be used. Clones of a library are spread onto plates, transferred to a substrate for screening, denatured and probed for the presence of desired sequences.

The nucleic acid sequences used in this invention will usually comprise at least about five codons (15 nucleotides), more usually at least about 7-15 codons, and most preferably, at least about 35 codons. This number of nucleotides is usually about the minimal length required for a successful HLS-5 fragment that is still capable of modulating transcription factors as described herein.

Techniques for nucleic acid manipulation are described generally, for example, in Sambrook et al., 1989, supra or Ausubel et al., 1992, Current Protocols in Molecular Biology. Reagents useful in applying such techniques, such as restriction enzymes and the like, are widely known in the art and commercially available from such vendors as New England BioLabs, Boehringer Mannheim, Amersham, Promega Biotec, US Biochemicals, New England Nuclear and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, the term "HLS-5 gene sequence" refers to the double-stranded DNA comprising the gene sequence or region, as well as either of the single-stranded DNAs comprising the gene sequence or region (i.e. either of the coding and non-coding strands).

As used herein, a "portion" of the HLS-5 gene sequence or region is defined as having a minimal size of at least about eight nucleotides, or preferably about 15 nucleotides, or more preferably at least about 25 nucleotides, and may have a minimal size of at least about 40 nucleotides.

HLS-5 polynucleotide or fragments thereof may be obtained via any known molecular technique. PCR is one such technique that may be used to obtain HLS-5 gene sequences. This technique may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid that contains one strand of each may be utilized. A mixture of nucleic acids may also be employed, or the nucleic acids produced in a previous amplification reaction described herein, using the same or different primers may be so utilise.

The specific nucleic acid sequence to be amplified, i.e., the HLS-5 gene sequence, may be a fraction of a larger molecule or can be present initially as a discrete molecule, so that the specific sequence constitutes the entire nucleic acid. It is not necessary that the sequence to be amplified is present initially in a pure form; it may be a minor fraction of a complex mixture, such as contained in whole human DNA.

DNA utilized herein may be extracted from a body sample, such as blood, tissue material and the like by a variety of techniques such as that described by Maniatis et al. 1982, supra. If the extracted sample has not been purified, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP and dTTP are added to the synthesis mixture, either separately or together with the primers; in adequate amounts and the resulting solution is heated to about 90°-100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"); and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions.

Thus, for example, if DNA polymerase is used as the agent, the temperature is generally no greater than about 40° C. Most conveniently the reaction occurs at room temperature.

The agent for polymerisation may be any compound or system which will function to accomplish the synthesis of primer extension products, including enzymes.

Suitable enzymes for this purpose include, for example, *E. coli* DNA polymerase I, Klenow fragment of *E. coli* DNA polymerase, polymerase muteins, reverse transcriptase, other enzymes, including heat-stable enzymes (i.e., those enzymes which perform primer extension after being subjected to temperatures sufficiently elevated to cause denaturation), such as Tag polymerase. Suitable enzyme will facilitate combination of the nucleotides in the proper manner to form the primer extension products that are complementary to each HLS-5 gene sequence nucleic acid strand. Generally, the synthesis will be initiated at the 3' end of each primer and proceed in the 5' direction along the template strand, until synthesis terminates, producing molecules of different lengths.

The newly synthesised HLS-5 strand and its complementary nucleic acid strand will form a double-stranded molecule under hybridizing conditions described above and this hybrid is used in subsequent steps of the process. In the next step, the newly synthesized HLS-5 double-stranded molecule is subjected to denaturing conditions using any of the procedures described above to provide single-stranded molecules.

The steps of denaturing, annealing, and extension product synthesis can be repeated as often as needed to amplify the target polymorphic gene sequence nucleic acid sequence to the extent necessary for detection. The amount of the specific nucleic acid sequence produced will accumulate in an exponential fashion. Amplification is described in "PCR. A Practical Approach", ILR Press, Eds. McPherson et al., 1992.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki et al., 1985, *Bio/Technology*, 3: 1008-1012), allele-specific oligonucleotide (ASO) probe analysis (Conner et al., 1983, *Proc. Natl. Acad. Sci. USA.,* 80: 278), oligonucleotide ligation assays (OLAs) (Landgren et al., 1988, *Science,* 241: 1007) and the like. Molecular techniques for DNA analysis have been reviewed (Landgren et al., 1988, *Science,* 242: 229-237).

Methods of obtaining HLS-5 polynucleotides of the present invention include PCR, as described herein and as commonly used by those of ordinary skill in the art. Alternative methods of amplification have been described and can also be employed as long as the HLS 5 gene sequence amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA. Another nucleic acid amplification technique is nucleic acid sequence-based amplification (NASBA) which uses reverse transcription and T7 RNA polymerase and incorporates two primers to target its cycling scheme. NASBA can begin with either DNA or RNA and finish with either, and amplifies to 108 copies within 60 to 90 minutes.

Alternatively, HLS-5 polynucleotides can be amplified by ligation activated transcription (LAT). LAT works from a single-stranded template with a single primer that is partially single-stranded and partially double-stranded. Amplification is initiated by ligating a cDNA to the promoter oligonucleotide and within a few hours, amplification is 108 to 109 fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest. Another nucleic acid amplification technique, ligase chain reaction (LCR), works by using two differently labelled halves of a sequence of interest that are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligonucleotide probe pairs, and the RCR fills and joins the gap, mimicking normal DNA repair. Nucleic acid amplification by strand displacement activation (SDA) utilizes a short primer containing a recognition site for Hinc II with short overhang on the 5' end that binds to target DNA. A DNA polymerase fills in the part of the primer opposite the overhang with sulphur-containing adenine analogs. Hinc II is added but only cuts the unmodified DNA strand. A DNA polymerase that lacks 5' exonuclease activity enters at the site of the nick and begins to polymerize, displacing the initial primer strand downstream and building a new one which serves as more primer. SDA produces greater than 107-fold amplification in 2 hours at 37° C. Unlike PCR and LCR, SDA does not require instrumented temperature cycling. Another amplification system useful in the method of the invention is the QB Replicase System. Although PCR is the preferred method of amplification if the invention, these other methods can also be used to amplify the HLS-5 gene sequence as described in the method of the invention.

Large amounts of the HLS-5 polynucleotides of the present invention may also be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines.

A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

HLS-5 polynucleotides of the invention may be incorporated into a recombinant replicable vector for introduction into a prokaryotic or eukaryotic host. Such vectors may typically comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Secretion signals may also be included where appropriate, whether from a native HLS-5 protein or from other receptors or from secreted polypeptides of the same or related species, which allow the protein to cross and/or lodge in cell membranes, and thus attain its functional topology, or be secreted from the cell. Such vectors may be prepared by means of standard recombinant techniques well known in the art and discussed, for example, in Sambrook et al., 1989 supra or Ausubel et al. 1992 supra.

An appropriate promoter and other necessary vector sequences will be selected so as to be functional in the host, and may include, when appropriate, those naturally associated with HLS-5 genes. Examples of workable combinations of cell lines and expression vectors are described in Sambrook et al., 1989 supra or Ausubel et al., 1992. Many useful vectors are known in the art and may be obtained from such vendors as Stratagene, New England Biolabs, Promega, Biotech, and others. Promoters such as the trp, lac and phage promoters, tRNA promoters and glycolytic enzyme promoters may be used in prokaryotic hosts.

Useful yeast promoters include promoter regions for metallothionein, phosphoglycerate kinase or other glycolytic enzymes such as enolase orglyceraldehyde-3-phosphate dehydrogenase, enzymes responsible for maltose and galactose utilization, and others. Vectors and promoters suitable for use in yeast expression are further described in Hitzeman et al., 1983, *Science*, 219, pages 620-625.

Appropriate non-native mammalian promoters might include the early and late promoters from SV40 or promoters derived from murine Moloney leukemia virus, mouse tumour virus, avian sarcoma viruses, adenovirus 11, bovine papilloma virus or polyoma. In addition, the construct may be joined to an amplifiable gene (e.g., DHFR) so that multiple copies of the gene may be made.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that a) confer resistance to antibiotics or other toxic substances, e.g. ampicillin, neomycin, methotrexate, etc.; b) complement auxotrophic deficiencies, or c) supply critical nutrients not available from complex media, e.g., the gene encoding D-alanine racemase for *Bacilli*. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection, or the vectors can be introduced directly into host cells by methods well known in the art, which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome); and other methods. The introduction of the polynucleotides into the host cell by any method known in the art, including, inter alfa, those described above, will be referred to herein as "transformation". The cells into which have been introduced nucleic acids described above are meant to also include the progeny of such cells.

Thus the present invention provides host cells transformed or transfected with a nucleic acid molecule of the invention. Preferred host cells include bacteria, yeast, mammalian cells, plant cells, insect cells, and human cells.

Illustratively, such host cells are selected from the group consisting of *E. coli, Pseudomonas, Bacillus, Streptomyces*, yeast, CHO, R1.1, B-W, L-M, COS 1, COS 7, BSC1, BSC40, BMT10, and Sf9 cells.

Large quantities of the NLS-5 polypeptides of the present invention may be prepared by expressing the HLS-5 polynucleotides or portions thereof in vectors or other expression vehicles in compatible prokaryotic or eukaryotic host cells. The most commonly used prokaryotic hosts are strains of *Escherichia coli*, although other prokaryotes, such as *Bacillus subtilis* or *Pseudomonas* may also be used.

Also provided are mammalian cells containing an HLS-5 polypeptide encoding DNA sequence and modified in vitro to permit higher expression of HLS-5 polypeptide by means of a homologous recombinational event consisting of inserting an expression regulatory sequence in functional proximity to the HLS-5 polypeptide encoding sequence. The expression regulatory sequence can be an HLS-5 polypeptide expression or not and can replace a mutant HLS-5 polypeptide regulatory sequence in the cell.

Thus, the present invention also provides methods for preparing an HLS-5 polypeptide comprising: (a) culturing a cell as described above under conditions that provide for expression of the HLS-5 polypeptide; and (b) recovering the expressed HLS-5 polypeptide. This procedure can also be accompanied by the steps of: (c) chromatographing the polypeptide using any suitable means known in the art; and (d) purifying the polypeptide by for example gel filtration.

Mammalian or other eukaryotic host cells, such as those of yeast, filamentous fungi, plant, insect, or amphibian or avian species, may also be useful for production of the proteins of the present invention. Propagation of mammalian cells in culture is per se well known. Examples of commonly used mammalian host cell lines are VERO and HeLa cells, Chinese hamster ovary (CHO) cells, and W138, BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics.

Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention.

In some embodiments the "transcription factor modulator" is a compound or composition capable of regulating the endogenous levels of HLS-5 and/or HLS-5 activity. In some embodiments, these compounds and compositions are termed "control agents". Control agents useful in the present invention may be located by standard assays. Protocols for carrying out such assays are well known to those of skill in the art and need not be described in great detail here. The term "control agent" or "drug candidate" or "modulator" or "modifying agent" or grammatical equivalents as used herein describes any molecule, eg., protein, oligopeptide, small organic molecule, polysaccharide, polynucleotide, etc., to be tested for the capacity to directly or indirectly control the expression of HLS-5 e.g., a nucleic acid or protein sequence. In some embodiments, the control agents will reduce the endogenous amount of HLS-5, while in other embodiments, the control agents will increase endogenous amount of HLS-5.

The term "drug candidates" encompass numerous chemical classes, though typically they are organic molecules, preferably small organic compounds having a molecular weight of more than 100 and less than about 2,500 daltons. Preferred small molecules are less than 2000, or less than 1500 or less than 1000 or less than 500 Daltons. Candidate control agents comprise functional groups necessary for Structural interaction with proteins, particularly hydrogen bonding, and typically include at least an amine, barbonyl, hydroxyl or carboxyl group, preferably at least two of the functional chemical groups. The candidate control agents often comprise cyclical carbon or heterocyclic structures and/or aromatic or polyaromatic structures substituted with one or more of the above functional groups. Candidate control agents are also found among biomolecules including peptides, saccharides, fatty acids, steroids, purines, pyrimidines, derivatives, structural analogs or combinations thereof. Particularly preferred are peptides.

The term "regulating" as used herein with reference to the endogenous levels of HLS-5 refers to the ability of the compound or composition to increase or decrease the endogenous levels of HLS-5 and/or HLS-5 activity as compared to the wild-type and/or normal levels. In some embodiments, control agents of the present invention that are capable of regulating the endogenous levels of HLS-5 and/or HLS-5 activity can be initially identified using in vitro cell based assays. For example, a system such as Chroma-Luc™, Luc™ or GFP™ reporter genes can be provided in multiple different cloning vector formats. The Basic vector versions are general-purpose reporter vectors based on the design, for example of the pGL3-Basic Vector, which lacks eukaryotic promoter and enhancer sequences, allowing cloning putative regulatory sequences, such as the HLS-5 promoter at the 5' end of the reporter gene. Expression of luciferase, or any reporter gene, activity in cells transfected with this "pGL3-Promoter Vector" depends on elements or compounds being able to induce directly or indirectly the expression through the cloned promoter of interest, such as the HLS5 promoter. In addition to the basic vector configuration, other systems such as the Chroma-Luc™ genes are available in a vector configuration containing an SV40 promoter and SV40 enhancer, similar to the pGL3-Control Vector. The presence of the SV40 promoter and enhancer sequences result in strong expression of luc+ in many types of mammalian cells. Thus this technology and any other vector modification is suitable for rapid quantitation in multiwell plates and in high-throughput applications to assay for compounds which are potentially capable of modifying the HLS-5 protein expression by measuring the reporter gene downstream of the HLS-5 promoter. These identified compounds can than be tested in cells with the endogenous HLS-5 promoter and protein expression assayed by such methods as Western Blots. In general, any luminometer capable of measuring filtered luminescence should be able to perform dual-colour assays and any scientist skilled in the art can reproduce these assays.

Once the transcription factor modulators eg HLS-5 polypeptide, HLS-5 polynucleotide in appropriate vector or compound/composition capable of regulating the endogenous levels of HLS-5 and/or HLS-5 activity, have been obtained they are then administered to a subject in need thereof in order to modulate transcription factor activity. Thus, in some embodiments, the present invention provides a method of treating a subject suffering from a "transcription factor-associated disorder" i.e. a disorder which is affected, by, controlled by or exacerbated by transcription factor activity and therefore, the step of administration assists in the treatment of the condition.

Generally, the terms "treating," "treatment" and the like are used herein to mean affecting a subject e.g. human individual or animal, their tissue or cells to obtain a desired pharmacological and/or physiological effect. The effect may be prophylactic in terms of completely or partially preventing the transcription factor-associated disorder or sign or symptom thereof, and/or may be therapeutic in terms of a partial or complete cure of the transcription factor-associated disorder. "Treating" as used herein covers any treatment of, or prevention of a condition associated with or exacerbated by transcription factor activity in a vertebrate, a mammal, particularly a human, and includes: (a) preventing the condition from occurring in a subject that may be predisposed to the transcription factor-associated disorder, but has not yet been diagnosed as having it; (b) inhibiting the transcription factor-associated disorder, i.e., arresting its development; or (c) relieving or ameliorating the condition, i.e., cause regression of the symptoms.

The term "subject" as used herein refers to an animal subject in which the modulation of transcription factor activity is desirable. The subject may be a human, or may be a domestic, companion or zoo animal. While it is particularly contemplated that the transcription factor modulator of the invention is suitable for use in medical treatment of humans, it is also applicable to veterinary treatment, including treatment of companion animals such as dogs and cats, and domestic animals such as horses, cattle and sheep, or zoo animals such as non-human primates, felids, canids, bovids, and ungulates.

The transcription factor modulator can be administered in various forms, depending on the condition to be treated and the age, condition and body weight of the subject, as is well known in the art. For example, where the transcription factor modulator is to be administered orally, it may be formulated as tablets, capsules, granules, powders or syrups; or for parenteral administration, it may be formulated as injections (intravenous, intramuscular or subcutaneous), drop infusion preparations or suppositories. For application by the ophthalmic mucous membrane route, it may be formulated as eye drops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent. Although the dosage will vary depending on the symptoms, age and body weight of the subject, the nature and severity of the condition to be treated or prevented, the route of administration and the form of the transcription factor modulator, in general, a daily dosage of from 0.01 to 2000 mg of the transcription factor modulators is recommended for an adult human subject, and this may be administered in a single dose or in divided doses.

An effective time for administering the transcription factor modulator needs to be identified. This can be accomplished by routine experiments. For example, in animals, the control of transcription factor activity by the transcription factor modulator can be assessed by administering the transcription factor modulator at a particular time of day and measuring the effect of the administration (if any) by measuring one or more indices associated with transcription factor activity, and comparing the post-treatment values of these indices to the values of the same indices prior to treatment.

The precise time of administration and/or amount of transcription factor modulator that will yield the most effective results in terms of efficacy of treatment in a given subject will depend upon the activity, pharmacokinetics, and bioavailability of a particular transcription factor modulator, physiological condition of the subject (including age, sex, disease type and stage, general physical condition, responsiveness to a given dosage and type of medication), route of administration, etc. However, the above guidelines can be used as the basis for fine-tuning the treatment, eg., determining the optimum time and/or amount of administration, which will require no more than routine experimentation consisting of monitoring the subject and adjusting the dosage and/or timing.

The phrases "pharmaceutically-effective amount" and "therapeutically-effective amount" as used herein means that amount of a transcription factor modulator, which is effective for producing some desired therapeutic effect, for example, the inhibition of transcription factor activity of a protein at a reasonable benefit/risk ratio applicable to any medical treatment.

The phrase "pharmaceutically acceptable" is employed herein to refer to those transcription factor modulators, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the transcription factor modulators from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminium hydroxide; (15) alginic acid, (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as colouring agents, release agents, coating agents, sweetening; flavouring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin; propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a transcription factor modulator(s) with the carrier and, optionally, one or more accessory ingredients. In general, the formulations are prepared by uniformly and intimately bringing into association a transcription factor modulator with liquid carriers, or finely divided solid carriers, or both, and then, if necessary, shaping the product.

Formulations suitable for oral administration may be in the form of capsules, cachets, pills, tablets, lozenges (using a flavoured basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatine and glycerine, or sucrose and acacia) and/or as mouth washes and the like, each containing a predetermined amount of a transcription factor modulator(s) as an active ingredient. A compound may also be administered as a bolus, electuary or paste.

In solid dosage forms for oral administration (capsules, tablets, pills, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) colouring agents. In the case of capsules, tablets and pills, the pharmaceutical compositions may also comprise buffering agents. Solid compositions of a similar type may also be employed as fillers in soft and hard-filled gelatine capsules using such excipients as lactose or milk sugars, as well as high molecular weight polyethylene glycols and the like.

A tablet may be made by compression or moulding, optionally with one or more accessory ingredients. Compressed tablets may be prepared using binder (for example, gelatine or hydroxypropylmethyl cellulose), lubricant, inert diluent, preservative, disintegrant (for example, sodium starch glycolate or cross-linked sodium carboxymethyl cellulose), surface-active or dispersing agent. Moulded tablets may be made by moulding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isodropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavouring, colouring, perfuming and preservative agents.

Suspensions, in addition to the active transcription factor modulator(s) may contain suspending agents as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

Dosage forms for the topical or transdermal administration of a transcription factor modulator(s) include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to transcription factor modulator(s), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a transcription factor modulator(s), excipients such as lactose, talc, silicic acid, aluminium hydroxide, calcium silicates and polyamide powder, or mixtures of these substances. Sprays can additionally contain customary propellants, such as chlorofluorohydrocarbons and volatile unsubstituted hydrocarbons, such as butane and propane.

The transcription factor modulator(s) can be alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizes vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a transcription factor modulator(s) to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more transcription factor modulator(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various anti-bacterial and anti-fungal agents, for example, paraben, chlorobutanol, phenol sorbic-acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminium monostearate and gelatine.

In some cases, in order to prolong the effect of a transcription factor modulator, it is desirable to slow the absorption of the agent from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered agent form is accomplished by dissolving or suspending the modulator in an oil vehicle.

Injectable depot forms are made by forming microencapsule matrices of transcription factor modulator(s) in biodegradable polymers such as polylactide-polyglycolide. Depending on the ratio of modulator to polymer, and the nature of the particular polymer employed, the rate of modulator release can be controlled. Examples of other biodegradable polymers include poly(orthoesters) and poly(anhydrides). Depot injectable formulations are also prepared by entrapping the modulator in liposomes or microemulsions which are compatible with body tissue.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a transcription factor modulator other than directly into the central nervous system, such that it enters the subjects system and, thus, is subject to metabolism and other like processes, for example, subcutaneous administration.

Another aspect of the invention provides a conjoint therapy wherein one or more other therapeutic agents are administered with the transcription factor modulator. Such conjoint treatment may be achieved by way of the simultaneous, sequential or separate dosing of the individual components of the treatment.

In some embodiments, a transcription factor modulator is conjointly administered with anti-cancer agents or other therapeutic agents known to be useful in the treatment of the condition being treated. For example, gene therapy using HLS-5 expression vector together with an anti-cancer agent.

In another illustrative embodiment, the subject control agents can be conjointly administered with a transcription factor agonist or antagonist.

As described supra, in some embodiments the HLS-5 polynucleotides and vectors of the invention for in vivo delivery and expression. This approach has also been called "gene therapy" and as such is well known in the art. Gene therapy protocols may involve administering a therapeutically-effective amount of a HLS-5 polynucleotide vector capable of directing expression of the HLS-5 polypeptide to a subject either before, substantially contemporaneously, with, or after influenza virus infection. Another approach that may be used alternatively or in combination with the foregoing is to isolate a population of cells, e.g., stem cells or immune system cells from a subject, optionally expand the cells in tissue culture, and administer a HLS-5 polynucleotide vector capable of directing expression of HLS-5 to the cells in vitro. The cells may then be returned to the subject. Optionally, cells expressing the HLS-5 polynucleotides can be selected in vitro prior to introducing them into the subject. In some embodiments of the invention a population of cells, which may be cells from a cell line or from an individual who is not the subject, can be used. Methods of isolating stem cells, immune system cells, etc., from a subject and returning them to the subject are well known in the art. Such methods are used, eg., for bone marrow transplant, peripheral blood stem cell transplant, etc., in patients undergoing chemotherapy.

In yet another approach, oral gene therapy may be used. For example, U.S. Pat. No. 6,248,720 describes methods and compositions whereby genes under the control of promoters are protectively contained in microparticles and delivered to cells in operative form, thereby achieving non-invasive gene delivery. Following oral administration of the microparticles, the genes are taken up into the epithelial cells, including absorptive intestinal epithelial cells, taken up into gut associated lymphoid tissue, and even transported to cells remote from the mucosal epithelium. As described therein, the microparticles can deliver the genes to sites remote from the mucosal epithelium, i.e. can cross the epithelial barrier and enter into general circulation, thereby transfecting cells at other locations.

As used herein, the term "condition" is interchangeably used with the term "transcription factor-associated disorder", which includes a disease, disorder, or condition, which is caused by or associated with the function of a transcription factor in a cell. A transcription factor-associated disorder includes a disease, disorder, or condition, which proceeds, directly or indirectly, via transcription factor-induced gene transcription.

At present there are a number of conditions/disorders known to be affected by aberrant transcription factor activity including, but not limited to, cancer (e.g. aberrant cellular apoptosis), viral infection, and Crohn's disease. Thus, for example, a transcription factor-associated disorder may be an NF-KB associated disorder, such as: (a) an ischemic disease, e.g., ischemic diseases of organs (e.g., ischemic heart diseases such as myocardial infarction, acute heart failure, chronic heart failure, ischemic brain diseases such as cerebral infarction, and ischemic lung diseases such as pulmonary infarction), aggravation of the prognosis of organ transplantation or organ surgery (e.g., aggravation of the prognosis of heart transplantation, cardiac surgery, kidney transplantation, renal surgery, liver transplantation, hepatic surgery, bone marrow transplantation, skin grafting, corneal transplantation, and lung transplantation), reperfusion disorders, and post-PTCA restenosis; (b) an inflammatory disease, e.g., nephritis, hepatitis, arthritis, acute renal failure, chronic renal failure, and arteriosclerosis; and (c) an autoimmune disease, e.g., rheumatism, multiple sclerosis, and Hashimoto's thyroiditis. An NF-KB containing transcription factor modulator of the present invention is particularly suited for the therapy and prophylaxis of reperfusion disorders in ischemic diseases, aggravation of the prognosis of organ transplantation or organ surgery, post-PTCA restenosis, cancer metastasis and invasion, and cachexia such as weight loss following the onset of a cancer.

A transcription factor-associated disorder may also be an androgen-associated disorder, i.e., a disease, disorder, or condition, which proceeds, directly or indirectly, via androgen receptor-induced gene transcription. Androgen associated disorders include benign prostatic hypertrophy, male pattern baldness, acne, idiopathic hirsutism, and Stein-Leventhal syndrome. Androgen associated disorders further include cancers whose growth is promoted by androgens eg prostate cancer, ovarian cancer, bladder cancer, colon cancer, liver cancer, endometrial cancer, pancreatic cancer, lung cancer, esophageal cancer, cancer of the larynx and breast cancer. Other androgen-associated disorders include androgen insensitivity syndromes, infertility, endometrial cancer, and X-linked spinal bulbar muscular atrophy (SMBA). Examples of partial androgen insensitivity syndromes include incomplete testicular feminization, Reifenstein syndrome, Lubs syndrome, Gilbert-Dreifus syndrome, and Rosewater syndrome.

A transcription factor-associated disorder may also be an estrogen receptor-associated disorder, i.e., a disease, disorder, or condition, which proceeds, directly or indirectly, via estrogen receptor-induced gene transcription. Examples of estrogen receptor-associated disorders include breast cancer, osteoporosis, endometriosis, cardiovascular disease, hypercholesterolemia, prostatic hypertrophy, prostatic carcinomas, obesity, hot flashes, skin effects, mood swings, memory loss, menopausal syndromes, hair loss (alopecia), type-II diabetes, Alzheimer's disease, urinary incontinence, GI tract conditions, spermatogenesis, disorders associated with plasma lipid levels, acne, hirsutism, other solid cancers (such as colon, lung, ovarian, testis, melanoma, CNS, and renal), multiple myeloma, cataracts, lymphoma, and adverse reproductive effects associated with exposure to environmental chemicals.

In other embodiments, the transcription associated disorder is a disorder associated with aberrant (abnormally increased or decreased) apoptotic processes. These include disorders associated with decreased apoptotic processes, eg., cellular proliferative disorders or cellular differentiative disorders, eg., cancer, autoimmune disorders, or psoriasis, and disorders associated with increased apoptosis, e.g., degenerative disorders (including neurodegenerative disorders such as Alzheimer's Disease, amyotrophic lateral sclerosis (ALS), Parkinson's disease, Alzheimer's disease, ischemic brain injury, and Huntington's disease), Glaucoma, Age-related macular degeneration (AMD), peripheral neuropathy, stroke, depression, Diamond-Blackfan Anemia (DBA), Fanconi Anemia (FA) Shwachman Diamond Syndrome (SDS), ischemic injury (myocardial infarction), and virus induced lymphocyte depletion (e.g., associated with HIV/AIDS).

Examples of cellular proliferative and/or differentiative disorders include cancer, eg., carcinoma, sarcoma, metastatic disorders or hematopoietic neoplastic disorders, eg., leukaemia's. A metastatic tumor can arise from a multitude of primary tumor types, including but not limited to those of prostate, colon, lung, breast and liver origin.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Additional examples of proliferative disorders include hematopoietic neoplastic disorders. As used herein, the term "hematopoietic neoplastic disorders" includes diseases involving hyperplastic/neoplastic cells of hematopoietic origin, eg., arising from myeloid, lymphoid or erythroid lineages, or precursor cells thereof. In some embodiments, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Other examples of proliferative and/or differentiative disorders include skin disorders. The skin disorder may involve the aberrant activity of a cell or a group of cells or layers in the dermal, epidermal, or hypodermal layer, or an abnormality in the dermal-epidermal junction.

Examples of skin disorders include psoriasis, psoriatic arthritis, dermatitis (eczema), e.g., exfoliative dermatitis or atopic dermatitis, pityriasis rubra pilaris, pityriasis rosacea, parapsoriasis, pityriasis lichenoiders, lichen planus, lichen nitidus, ichthyosiform dermatosis, keratodermas, dermatosis, alopecia greata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as atopic dermatitis, allergic dermatitis, seborrheic dermatitis or solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; keratitis and viral infections Thus, for example, a transcription factor-associated disorder may be an NF-KB associated disorder, such as: (a) an ischemic disease, e.g., ischemic diseases of organs (e.g., ischemic heart diseases such as myocardial infarction, acute heart failure, chronic heart failure, ischemic brain diseases such as cerebral infarction, and ischemic lung diseases such as pulmonary infarction), aggravation of the prognosis of organ transplantation or organ surgery (e.g., aggravation of the prognosis of heart transplantation, cardiac surgery, kidney transplantation, renal surgery, liver transplantation, hepatic surgery, bone marrow transplantation, skin grafting, corneal transplantation, and lung transplantation), reperfusion disorders, and post-PTCA restenosis; (b) an inflammatory disease, e.g., nephritis, hepatitis, arthritis, acute renal failure, chronic renal failure, and arteriosclerosis; and (c) an autoimmune disease, e.g., rheumatism, multiple sclerosis, and Hashimoto's thyroiditis. An NF-KB containing transcription factor modulator of the present invention is particularly suited for the therapy and prophylaxis of reperfusion disorders in ischemic diseases, aggravation of the prognosis of organ transplantation or organ surgery, post-PTCA restenosis, cancer metastasis and invasion, and cachexia such as weight loss following the onset of a cancer.

The present invention also provides assays that are suitable for identifying substances that bind to HLS-5 polypeptides (reference to which includes homologues, variants, derivatives and fragments as described above). In addition, assays are provided that are suitable for identifying substances that interfere with HLS-5 binding to cellular components involved in sumoylation, for example proteins identified in yeast two-hybrid screens as interacting with HLS-5. Such assays are typically in vitro. Assays are also provided that test the effects of candidate substances identified in preliminary in vitro assays on intact cells in whole cell assays.

For example, a substance that alters transcription factor activity as a result of an interaction with HLS-5 polypeptides may do so in several ways. It may directly disrupt the binding of HLS-5 to a cellular component of the cell cycle machinery by, for example, binding to HLS-5 and masking or altering the site of interaction with the other component. Candidate substances of this type may conveniently be preliminarily screened by in vitro binding assays as, for example, described below and then tested, for example in a whole cell assay as described below.

Methods to screen potential agents for their ability to disrupt or moderate ubiquitin ligase expression and activity can be designed based on its known and potential substrates. For example, candidate compounds can be screened for their ability to modulate the interaction of an HLS-5 and Skp1, or the specific interactions of Skp2 With E2F-1, Skp2 with Cks1, Skp2 with Cks1 and p27, or the FBP1/Cul1/Skp1 complex with β-catenin. In principle, many methods known to those of skill in the art, can be readily adapted in designed the assays of the present invention.

The screening assays of the present invention also encompass high-throughput screens and assays to identify modulators of HLS-5 expression and activity. In accordance with this embodiment, the systems described below may be formulated into kits. To this end, cells expressing HLS-5 and components of the ubiquitin ligase complex and the ubiquitination pathway, or cell lysates, thereof can be packaged in a variety of containers, e.g., vials, tubes, microtitre well plates, bottles, and the like. Other reagents can be included in separate containers and provided with the kit; e.g., positive control samples, negative control samples, buffers, cell culture media, etc.

The invention provides screening methodologies useful in the identification of proteins and other compounds which bind to, or otherwise directly interact with, the HLS-5 genes and their gene products. Screening methodologies are well known in the art (see eg., PCT International Publication No. WO 96/34099, published Oct. 31, 1996, which is incorporated by reference herein in its entirety). The proteins and compounds include endogenous cellular components which interact with the identified genes and proteins in vivo and which, therefore, may provide new targets for pharmaceutical and therapeutic interventions, as well as recombinant, synthetic, and otherwise exogenous compounds which may have binding capacity and, therefore, may be candidates for pharmaceutical agents. Thus, in one series of embodiments, cell lysates or tissue homogenates may be screened for proteins or other compounds which bind to one of the normal or mutant HLS-5 genes and HLS-5 proteins.

Alternatively, any of a variety of exogenous compounds, both naturally occurring and/or synthetic (e.g., libraries of small molecules or peptides), may be screened for binding capacity. All of these methods comprise the step of mixing an HLS-5 protein or fragment with test compounds, allowing time for any binding to occur, and assaying for any bound complexes. All such methods are enabled by the present disclosure of substantially pure HLS-5 proteins, substantially pure functional domain fragments, fusion proteins, antibodies, and methods of making and using the same.

As mentioned previously, when administered to cells or when its expression levels are high, HLS-5 reduces levels of PIAS1, UB1, UBC9 and SUMO-1, resulting in a reduction of the overall SUMOylation of some protein targets and the induction of others. Thus in vivo SUMOylation assay is one test for the effect of candidate compounds on the HLS-5 transcription factor modulator of the present invention and this can be done by the administration a variant of HeLa or COS cell, for example, etc. and determine whether cells have altered levels of SUMOylation of individual protein products by western analysis.

In some embodiments, the control agents of the present invention relate to the use of RNA interference (RNAi) to reduce expression of one or more miRNAs encoded by the HLS-5. RNAi constructs comprise double stranded RNA that can specifically block expression of a target gene e.g. HLS-5. "RNA interference" or "RNAi" is a term initially applied to a phenomenon observed in plants and worms where double-stranded RNA (dsRNA) blocks gene expression in a specific and post-transcriptional manner. RNAi provides a useful method of inhibiting gene expression in vitro or in vivo. RNAi constructs can comprise either long stretches of dsRNA identical or substantially identical to the HLS-5 nucleic acid sequence or short stretches of dsRNA identical to or substantially identical to only a region of the HLS-5 nucleic acid sequence.

As used herein, the term "RNAi construct" is a generic term including small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo. In certain embodiments, the RNAi constructs are non-enzymatic nucleic acids.

Optionally, the RNAi constructs contain a nucleotide sequence that hybridizes under physiologic conditions of the cell to the nucleotide sequence of at least a portion of the mRNA transcript for the HLS-5 gene. The double-stranded RNA need only be sufficiently similar to natural RNA so that it has the ability to mediate RNAi. Thus, the RNAi constructs described herein have the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 base pairs, or 1 in 10 base pairs, or 1 in 20 base pairs, or 1 in 50 base pairs. Mismatches in the centre of the siRNA duplex are most critical and may essentially abolish cleavage of the HLS-5 RNA. In contrast, nucleotides at the 3' end of the siRNA strand that is complementary to the HLS-5 RNA do not significantly contribute to specificity of the target recognition. Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90%, 95%, 96%, 97%, 98%, or 99% sequence identity, or even 100% sequence identity, between the inhibitory RNA and the portion of the target gene is preferred. Alternatively, the duplex region of the RNA may be defined functionally as a nucleotide sequence that is capable of hybridizing under specified conditions with a portion of the target gene transcript (e.g., 400 mM NaCl, 40 mM PIPES pH 6.4, 1 mM EDTA, 50@C. or 70@C. hybridization for 12-16 hours; followed by washing).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

The subject RNAi constructs can be "small interfering RNAs" or "siRNAs." These nucleic acids are around 19-30 nucleotides in length, and even more preferably 21-23 nucleotides in length. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group. In certain embodiments, the siRNA constructs can be generated by processing of longer double-stranded RNAs, for example, in the presence of the enzyme dicer.

Alternatively, the RNAi construct is in the form of a hairpin structure (referred to as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., 2002, *Genes Dev*, 16:948-58; McCaffrey et al., 2002, *Nature*, 418:38-9; McManus et al., 2002, *RNA*, 8:842-50; Yu et al., 2002, *Proc Natl Acad Sci USA*, 99:6047-52). Preferably, such hairpin RNAs are engineered in cells or in an animal to ensure continuous and stable suppression of the HLS-5. It is known in the art that siRNAs can be produced by processing a hairpin RNA in the cell.

In another embodiment, the control agents are ribozyme molecules designed to catalytically cleave HLS-5 mRNA transcripts to prevent translation of mRNA (see, e.g., PCT International Publication WO90/11364, published Oct. 4, 1990; Sarver et al., 1990, *Science* 247:1222-1225; and U.S. Pat. No. 5,093,246). While ribozymes that cleave mRNA at site-specific recognition sequences can be used to destroy HLS-5 mRNAs, the use of hammerhead ribozymes is preferred. Hammerhead ribozymes cleave mRNAs at locations dictated by flanking regions that form complementary base pairs with the target mRNA. The sole requirement is that the target mRNA has the following sequence of two bases: 5'-UG-3'. The construction and production of hammerhead ribozymes is well known in the art and is described more fully in Haseloff and Gerlach, 1988, *Nature*, 334:585-591. The ribozymes of the present invention also include RNA endoribonucleases (hereinafter "Cech-type ribozymes") such as the one which occurs naturally in Tetrahymena thermophila (known as the IVS or L-19 IVS RNA) and which has been extensively described (see, e.g., Zaug et al., 1984, *Science*, 224:574-578; Zaug and Cech, 1986, *Science*, 231:470-475; Zaug et al., 1986, *Nature*, 324:429-433; published International patent application No. WO88/04300 by University Patents Inc.; Been and Cech, 1986, *Cell*, 47:207-216).

In another embodiment, the control agents are antisense nucleic acids which can readily be synthesized using recombinant means, or are synthesized in vitro. Equipment for such synthesis is sold by several vendors, including Applied Bio-systems. The preparation of other oligonucleotides such as phosphorothioates and alkylated derivatives is also well known to those of skill in the art.

Antisense molecules as used herein include anti-sense or sense oligonucleotides. Sense oligonucleotides can, eg., be employed to block transcription by binding to the anti-sense strand. The anti-sense and sense oligonucleotide comprise a single-stranded nucleic acid sequence (either RNA or DNA) capable of binding to target mRNA (sense) or DNA (anti-sense) sequences for PKC isozyme molecules. Anti-sense or sense oligonucleotides, according to the present invention, comprise a fragment generally at least about 14 nucleotides, preferably from about 14 to 30 nucleotides. The ability to derive an anti-sense or a sense oligonucleotide, based upon a cDNA sequence encoding a given protein is described in, eg., Stein & Cohen (*Cancer Res.* 48:2659 (1988 and van der Krol et al. 1988, *Bio Techniques,* 6:958).

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The following examples, which describe exemplary techniques and experimental results, are provided for the purpose of illustrating the invention, and should not be construed as limiting.

EXAMPLE 1

Co-Association of Protein Inhibitors of Activated Stat (PIAS) and the E3-Ligase HLS-5

Using full-length HLS5 as bait, a yeast two-hybrid screen was performed, which identified the protein inhibitor of activated Stat1 (PIAS1) as a novel HLS5 binding protein. In order to further characterize this interaction, deletion mutants of the different functional domains of the HLS5 protein were tested for their ability to bind to PIAS1. FIG. 1 shows that in the absence of the N terminal portion of HLS5 the interaction was lost and that the CC domain is essential for interaction between these two proteins.

Figure 2:
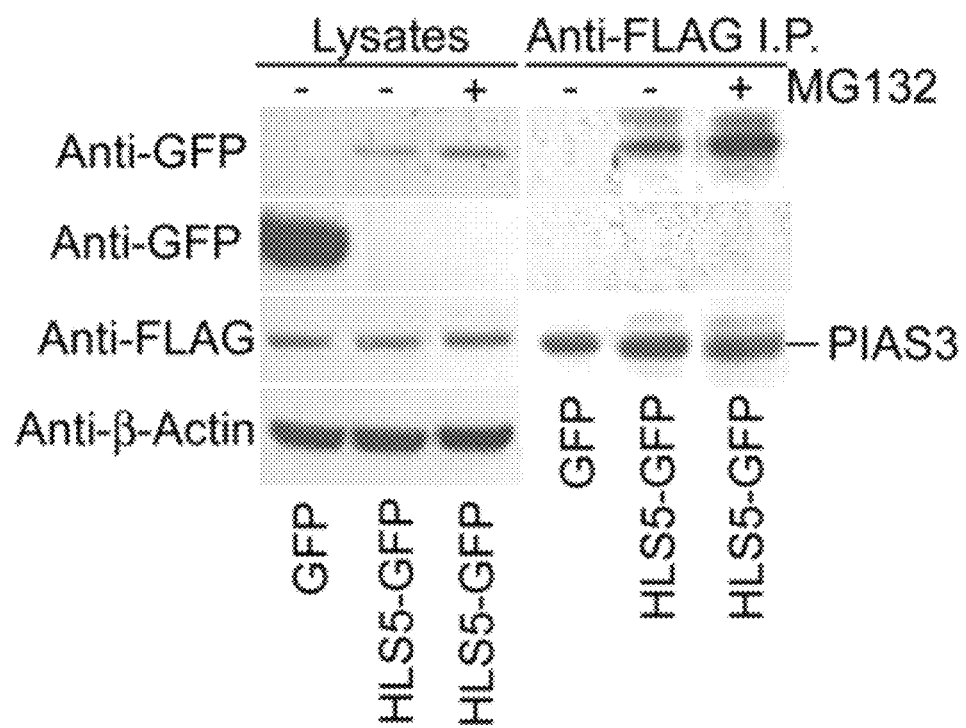
FIG. 2 represents a Western blot that shows the in vivo association of PIAS1 with HLS-5 by co-immunoprecipitation.

The in vivo association between HLS5 and PIAS was investigated by co-immunoprecipitation assays. FIG. 2 shows that co-transfection of Flag-tagged PIAS3 and HLS5-GFP, followed by immunoprecipitation with antibodies to GFP, resulted in the co-immunoprecipitation of Flag-PIAS3 with HLS5. This co-precipitation was enhanced by exposure of the cells to the proteasomal inhibitor MG132. These results demonstrate that HLS5 and PIAS interact, albeit transiently, in vivo.

In order to asses the localization of these two proteins, COS7 cells were transfected with FLAG-PIAS1 or FLAG-PIAS3 in the presence of HLS-5-GFP. Following incubation of the cells in the presence or absence of proteasome inhibitor MG132, the cells were subjected to fluorescence microscopy.

Figure 3:
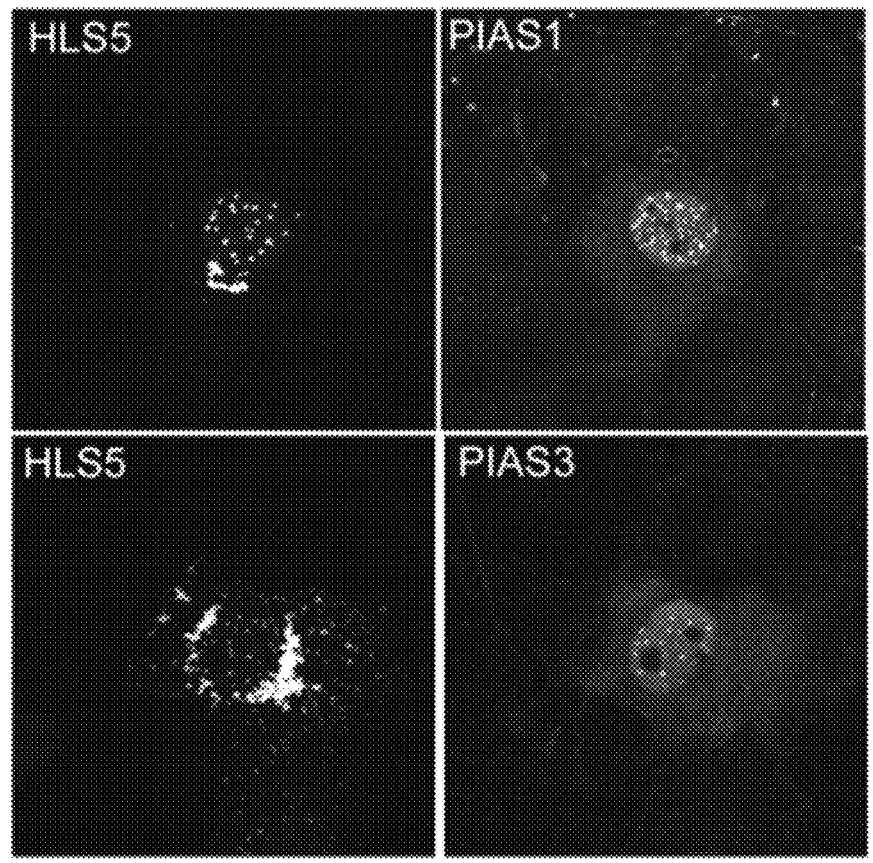
FIG. 3 represents fluorescence microscopy images that demonstrate extensive FLAG-PIAS1 colocalisation with HLS-5 at nuclear foci when proteosomal degradation is inhibited.

As shown in FIG. 3, FLAG-PIAS1 and FLAG-PIAS3 colocalised with HLS-5 at nuclear foci. This co-localisation was increased by incubation of the cells with proteaosomal inhibitor MG132. These experiments demonstrate that, in addition to the molecular interaction between HLS5 and PIAS family members, these proteins colocalize at sites of transcriptional regulation.

EXAMPLE 2

Physical and Functional Targeting of PIAS by HLS5

Figure 4:
FIG. 4 represents a Western blot that indicates a reduction of PIAS1 expression occurs when PIAS1 and HLS5 are co-transfected into COS cells.

To assess the biological significance of HLS-5 co-localisation and interaction with PIAS, the levels of PIAS expression and PIAS activity following co-transfection of cells with PIAS and HLS5 plasmid constructs were examined. As shown in FIG. 4, expression of exogenous HLS5, resulted in a specific reduction of the transfected PIAS1 protein level.

In light of the role of PIAS in transcriptional regulation, the modulation of PIAS levels by HLS-5 could influence gene expression.

Figure 5:
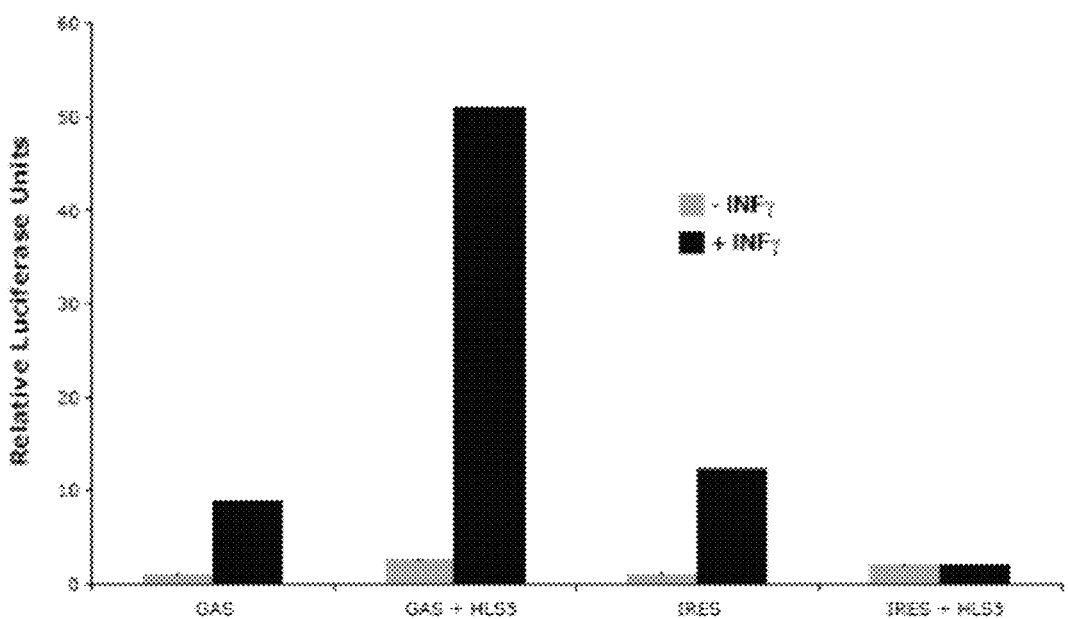
FIG. 5 presents luciferase promoter reporter activity indicating that introduction of exogenous HLS-5 into Hela cells strongly activates the transcriptional response to interferon ligands from the GAS promoter, but not the ISRE promoter.

PIAS1 was first isolated as Protein Inhibitor of Activated STAT1. To assay PIAS activity, the γ-interferon activated sequence (GAS) and interferon sequence response element (ISRE) luciferase reporters of STAT-mediated transcription were used. As shown in FIG. 5, expression of exogenous HLS5 in Hela cells greatly increased the transcriptional activity of the GAS promoter element, but had no discernable effect on the ISRE promoter. These results demonstrate that HLS5 operates as a specific transcriptional activator of the JAK/STAT signaling cascades.

Figure 6:
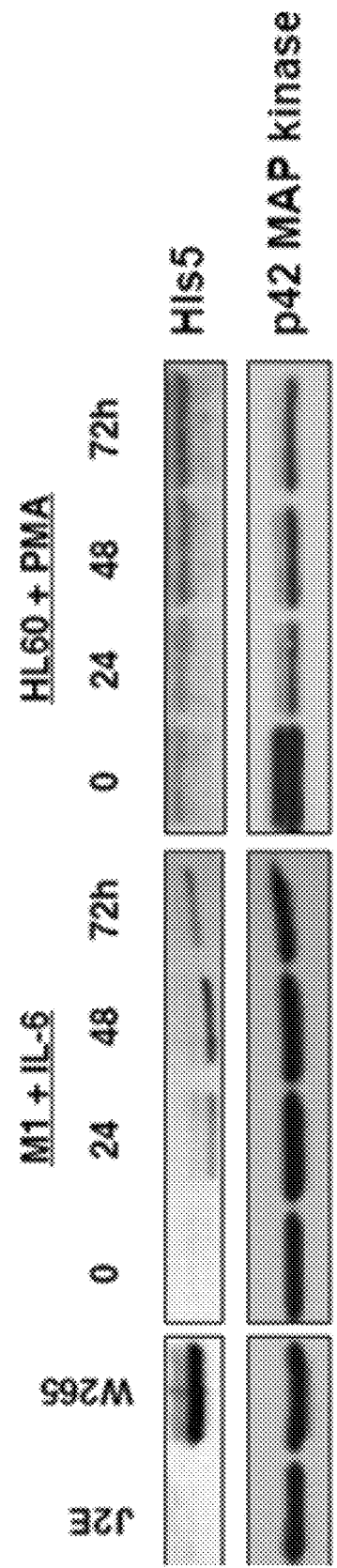
FIG. 6 represents Western blots that indicate that IL-6 in M1 myeloid cells, and PMA in HL-60 cells, strongly increase HLS-5 protein expression.

PIAS1 levels have been shown to be lower in more mature macrophages suggesting that its reduction is required to allow STAT1 to play its central role in this differentiation process (Coccia et al., 2002, *Cell Signal,* 14(6): p537-45). In FIG. 6, it is shown that factors that induce myeloid differentiation, such as IL-6 in M1 myeloid cells and PMA in HL-60 cells, caused a significant increase in HLS5 protein expression. STAT1 and STAT3 have long been reported to undergo activation via interferon-γ, and interleukin-6 family members (IL-6, CT-1 or LIF) signaling. This may be explained by our finding that HLS-5 can target PIAS, thereby resulting in STAT activation and a diverse set of STAT-mediated cellular responses to cytokines, such as apoptosis, cell cycle control, and differentiation.

These results identify PIAS as a target of HLS5. Since HLS5 suppresses PIAS protein levels and PIAS affects transcription, it can be derived that HLS5 plays a role in cell proliferation, migration, and differentiation by affecting PIAS-mediated regulation of STATs, and other transcription factors including NF-KB/IKB and p53.

EXAMPLE 3

Auto-Ubiquitination of HLS5

Figure 7:
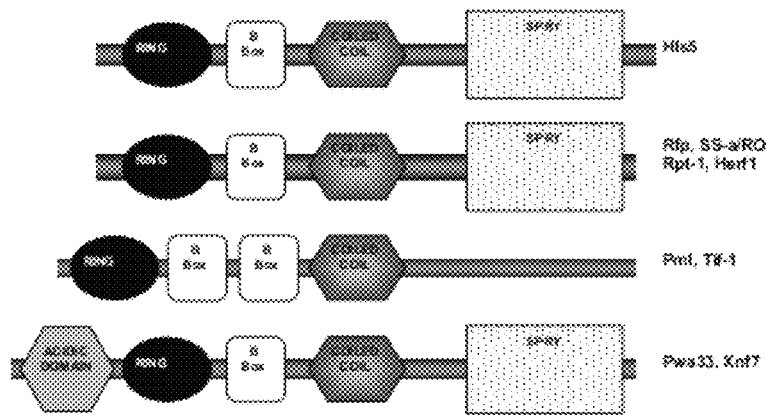
FIG. 7a shows the structural domains of HLS5, while FIG. 7b describes human TRIM/RBCC proteins with E3 activity in vitro or in vivo.
FIG. 7c shows multiple overlapping clones from a single gene, encoding a protein alternatively named UBC9, Cezanne, UBA52.
Figure 8:
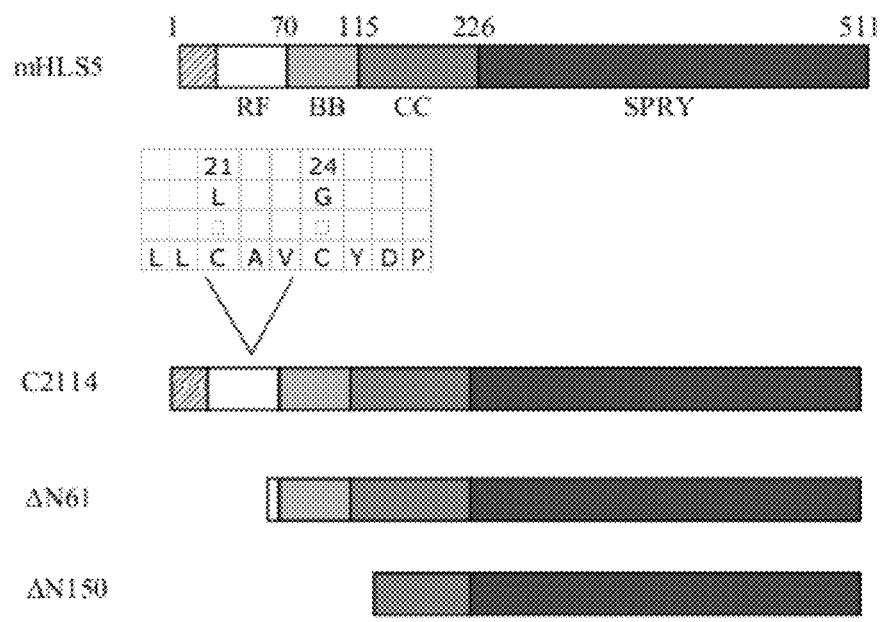
FIG. 8 represents Western blots of cell lysates (bottom panel) and HLS5 immunoprecipitates from HA-Ubiquitin expressing cells (top panel). Changes in the high-molecular-weight anti-HA-signal in the top panel highlight the role of the RING-finger motif in auto-ubiquitination.
Figure 8:
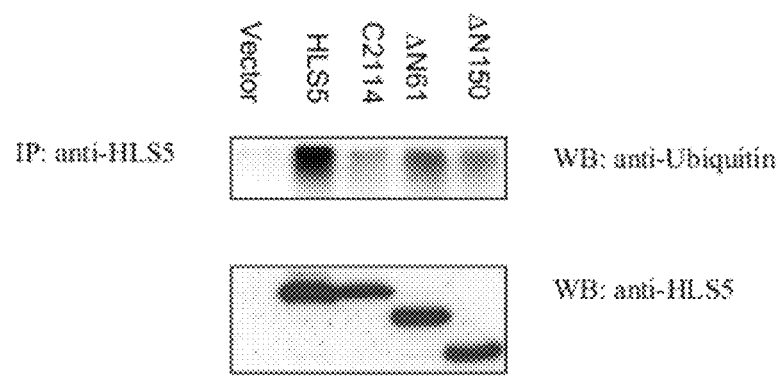

HLS5 is an RBCC protein, which is part of a large protein family, representing a class of single protein RING finger ubiquitin E3 ligases. FIG. 7 shows the structural domains of HLS5 and describes other human TRIM/RBCC proteins with E3 ubiquitin ligase activity in vitro or in vivo. As shown in FIG. 8, it was examined whether HLS5 also exhibits E3 ubiquitin ligase activity. This was done by assay of HLS-5 auto-ubiquitination in vivo. It was found that HLS5 undergoes auto-ubiquitination, as evidenced by high-molecular-weight products on anti-HA-ubiquitin Western blots of immunoprecipitated full-length HLS5, relative to RING deleted (ΔN61, ΔN150) or inactivated (C2124) HLS5.

EXAMPLE 4

PIAS as an E3 Ligase Substrate of HLS-5

Figure 9:
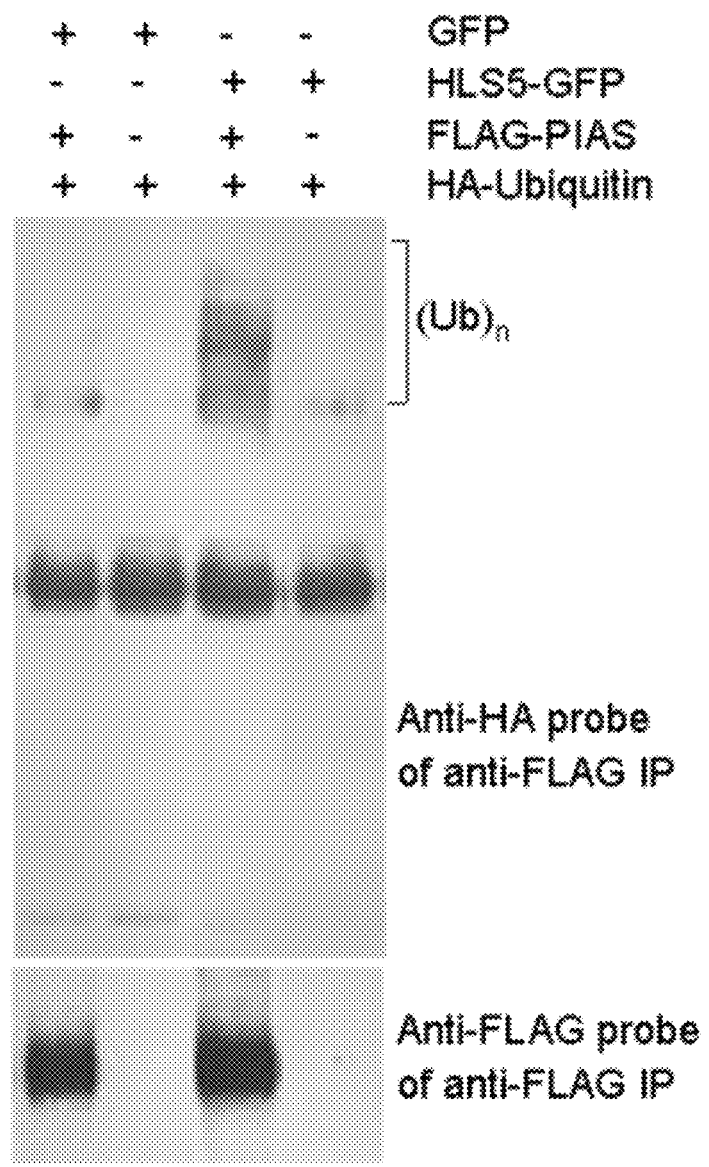
FIG. 9 represents Western blots of FLAG-PIAS immunoprecipitated from HA-Ubiquitin expressing cells, and shows that in the presence of exogenous HLS-5, the transfected PIAS1 becomes poly-ubiquitinated.

Since example 2 shows that HLS5 can reduce the levels of PIAS1 in vivo, it was also examined whether HLS5 indeed ubiquitinates PIAS1. Following transfection of the cells with Flag-PIAS1 and HA-tagged ubiquitin, PIAS1 was immunoprecipitated and ubiquitination determined by anti$_{13}$HA-Western blot. As shown in FIG. 9, the presence of HLS5-GFP, but not GFP, resulted in ubiquitination of PIAS.

Thus, it was found that HLS5 and PIAS are targeted to transcription regulatory sites in the nucleus. Further, Hls5 and PIAS physically interact, leading to ubiquitination and proteasomal targeting of PIAS. The resulting decrease, in PIAS levels leads to increased transcription by STATs and other factors regulated by PIAS.

EXAMPLE 5

Targeting of HLS-5 by siRNA-Mediated Inhibition of HLS5 Expression

The discovery of RNA interference (RNAi) in eukaryotic cells has been the major recent breakthrough in molecular and cell biology. Small interfering RNA (siRNA) and microRNA (miRNA) are small RNAs of 18-25 nucleotides (nt) in length that play important roles in regulating gene expression. They are incorporated into an RNA-induced silencing complex (RISC) and serve as guides for silencing their corresponding target mRNAs based on complementary base-pairing.

Knock-down by siRNA-mediated targeting of transcripts has emerged as one of the most important new technological developments in biomedical research. This technology allows examination of the role and function of target genes by knock-down, rather than by over-expression. This greatly decreases the possibility for experimental artefacts. Further, by permitting selective silencing of gene expression, siRNAs also hold great potential as therapeutic agents. In order to apply this technology to HLS5, pooled RNA oligonucleotides were tested for their ability to knock-down HLS5 protein levels in cells. This knock-down was assayed following expression of GFP-tagged HLS5 in Cos cells. Expression of the HLS5-GFP in Cos cells permitted the assaying of its expression by anti-GFP Western blotting. An advantage of this experimental system is that it could readily be tested using pre-validated siRNAs directed against GFP.

Figure 10:
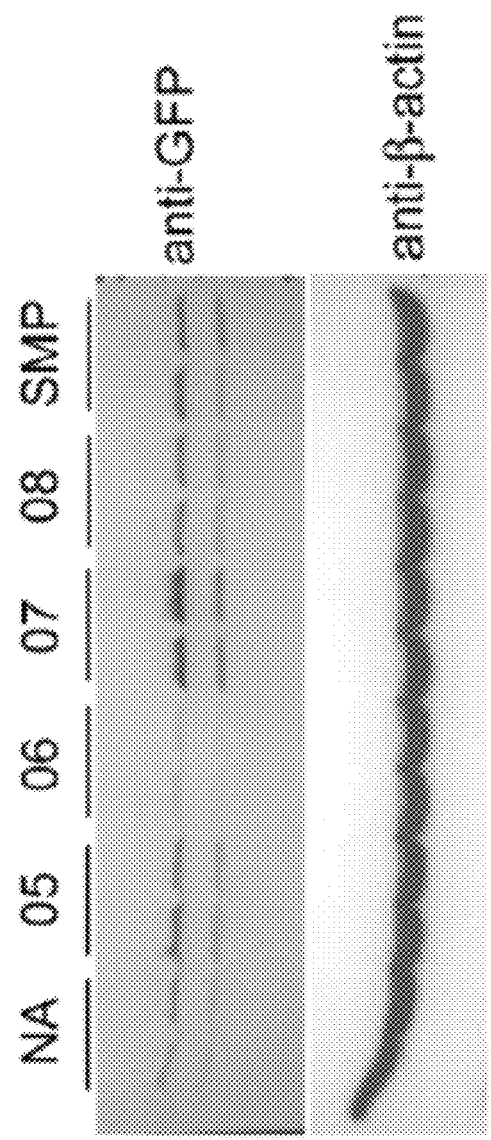
FIG. 10 represents Western blots indicating that oligo 06 reduces GFP-HLS5 levels, relative to $\beta$-actin

Using this assay system we identified a second-generation siRNA Smartpool (Dharmacon D-006952) that could knock-down HLS5-GFP levels (RMS, experiment #151). This knock-down result was developed further by examination of the activity of the individual RNA oligonucleotides contained in this Smartpool. Using the same HLS5-GFP assay system, it was found that oligo 06 reproducibly knocked-down GFP-HLS5 levels (see FIG. 10). This result paves the way for the use of HLS5 siRNA to modulate HLS5 functions.

The invention claimed is:

1. A method of identifying substances that alter transcription factor activity comprising:
   (i) providing a cell expressing an HLS-5 polynucleotide encoding an HLS-5 polypeptide;
   (ii) contacting said cell with a candidate substance suspected of being able to alter transcription factor activity and measuring the binding of HLS-5 to a moiety selected from the group consisting of: Skp1, Skp2 with E2F-1, Cks1 and/or p27; and
   (iii) comparing the ability of HLS-5 to bind a moiety in step (ii) to the level of the ability of HLS-5 to bind a moiety in a cell not contacted with said candidate substance;
   wherein a reduction in said HLS-5 binding to a moiety in step (ii) compared to step (iii) is indicative of a candidate substance that alters the transcription factor activity of HLS-5.

2. The method of claim 1, wherein said substance is a ubiquitin ligase.

3. The method of claim 1, wherein the HLS-5 polynucleotide is selected from the group consisting of:
   (a) polynucleotides comprising the nucleotide sequence set out in SEQ ID NO:1, SEQ ID NO:3 or SEQ ID NO:5;
   (b) polynucleotides comprising a nucleotide sequence capable of hybridizing selectively to the nucleotide sequence set out in SEQ ID NO:1, SEQ ID NO:3 or SEQ ID NO:5; and
   (c) polynucleotides comprising a polynucleotide sequence which is degenerate as a result of the genetic code to the polynucleotides defined in (a) or (b).

4. The method of claim 3, wherein the HLS-5 polynucleotide encodes a polypeptide comprising the sequence set out in SEQ ID NO: 2 or a polypeptide encoded by a nucleotide sequence which selectively hybridizes to the nucleotide sequence set out in SEQ ID NO: 1.

5. The method of claim 3, wherein the HLS-5 polynucleotide encodes a polypeptide comprising the sequence set out in SEQ ID NO: 4 or a polypeptide encoded by a nucleotide sequence which selectively hybridizes to the nucleotide sequence set out in SEQ ID NO: 3.

6. The method of claim 3, wherein the HLS-5 polynucleotide encodes a polypeptide comprising the sequence set out in SEQ ID NO: 6 or a polypeptide encoded by a nucleotide sequence which selectively hybridizes to the nucleotide sequence set out in SEQ ID NO: 5.

7. The method of claim 3, wherein the HLS-5 polynucleotide is expressed by a vector.

* * * * *

UNITED STATES PATENT AND TRADEMARK OFFICE
CERTIFICATE OF CORRECTION

| | | |
|---|---|---|
| PATENT NO. | : 8,778,633 B2 | Page 1 of 1 |
| APPLICATION NO. | : 13/310196 | |
| DATED | : July 15, 2014 | |
| INVENTOR(S) | : Lalonde et al. | |

It is certified that error appears in the above-identified patent and that said Letters Patent is hereby corrected as shown below:

On the title page, Item [73], delete "Molecular Discover Systems" and insert --Molecular Discovery Systems--.

Signed and Sealed this
Seventh Day of October, 2014

Michelle K. Lee
*Deputy Director of the United States Patent and Trademark Office*